United States Patent [19]

Nelms et al.

[11] 4,365,290
[45] Dec. 21, 1982

[54] COMPUTER SYSTEM WITH POWER CONTROL CIRCUIT

[75] Inventors: George E. Nelms, Edina; Thomas C. Barthel, Becker; William J. Bergland, Fridley, all of Minn.

[73] Assignee: Medtronic, Inc., Minneapolis, Minn.

[21] Appl. No.: 19,625

[22] Filed: Mar. 12, 1979

[51] Int. Cl.³ .................. G06F 01/04; A61N 01/36
[52] U.S. Cl. .................. 364/200; 365/227; 128/419 P; 364/707
[58] Field of Search ... 364/200 MS File, 900 MS File, 364/707; 365/226, 227; 128/419 P

[56] References Cited

U.S. PATENT DOCUMENTS

| | | | |
|---|---|---|---|
| 3,643,219 | 2/1972 | Heimann | 364/200 |
| 3,703,710 | 11/1972 | Kubo et al. | 365/226 |
| 3,805,796 | 4/1974 | Terry, Jr. et al. | 128/419 P |
| 3,833,005 | 9/1974 | Wingrove | 128/422 |
| 3,922,526 | 11/1975 | Cochran | 364/707 |
| 3,941,989 | 3/1976 | McLaughlin et al. | 364/900 |
| 3,956,740 | 5/1976 | Jones et al. | 364/900 |
| 3,976,995 | 8/1976 | Sebestyen | 340/337 |
| 4,089,062 | 5/1978 | McElroy et al. | 364/900 |
| 4,130,899 | 12/1978 | Bowman et al. | 365/226 |
| 4,151,611 | 4/1979 | Sugawara et al. | 365/227 |

*Primary Examiner*—Gareth D. Shaw
*Assistant Examiner*—Eddie P. Chan
*Attorney, Agent, or Firm*—R. Lewis Gable; John L. Rooney; Joseph F. Breimayer

[57] ABSTRACT

A digital computer system is described as comprising an input data circuit, a processor for executing a program stored in a memory to process the inputted data, a depletable energy source (e.g., a battery) for energizing the elements of the computer system, and a power control circuit for selectively controlling the drain imposed upon the energy source in accordance with the data input into the system and the program executed by the processor. In an illustrative embodiment of this invention, the power control circuit is operative in at least three modes of operation, namely off/rest, power down, and operating. In the off/rest mode, the power control circuit imposes a minimum power drain upon the depletable energy source. An operator may manipulate a switch or actuation means to apply a transition signal to the power control, whereby the computer system is disposed from its off/rest mode to its power down mode. In the power down mode, the control circuit applies power at an intermediate level to the data input means. In an illustrative embodiment of this invention, the data input means includes a keyboard and a decoder for providing a signal indicative that one of the keys has been depressed. Upon actuation of the key, a data available signal DA is transmitted to the power control circuit, whereby the computer system is disposed in its operating mode, wherein all of the elements of the computer system are energized at a high power level. In its operating mode, the processor and its memory are fully energized to execute the stored program.

22 Claims, 19 Drawing Figures

FIG. 1.
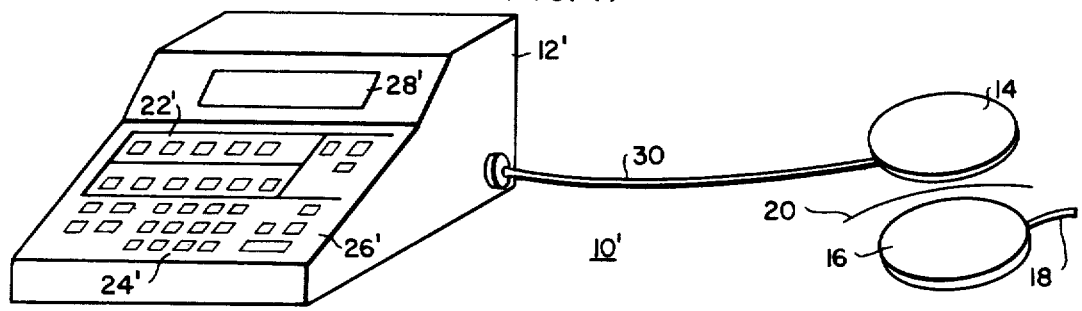
FIG. 2.
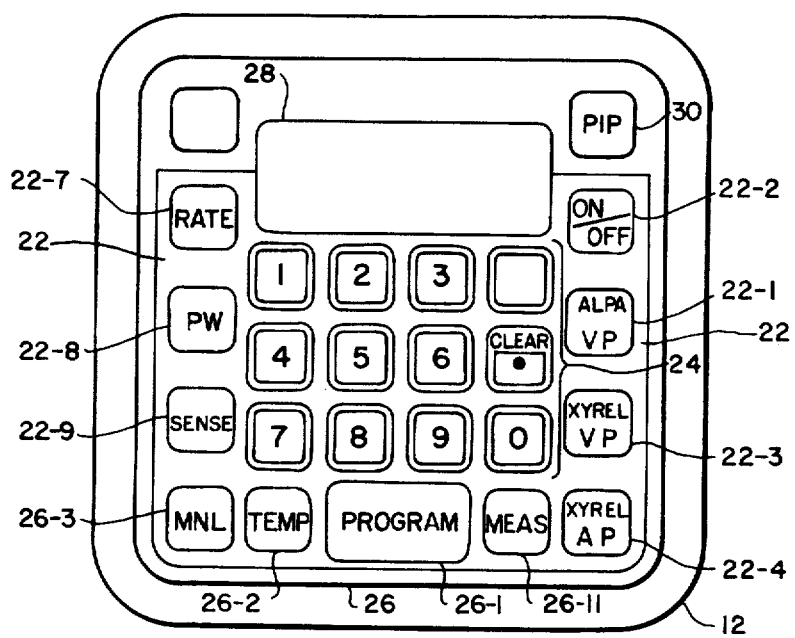
FIG. 3.
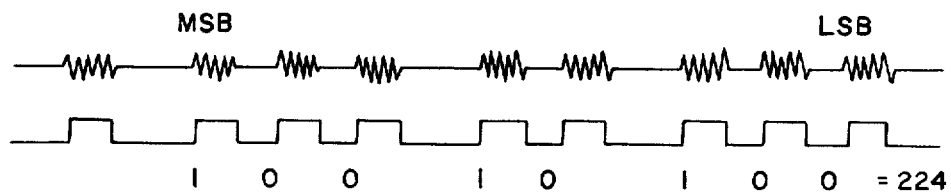
FIG. 4.
| PARAMETER | DATA | ACCESS | PARITY |

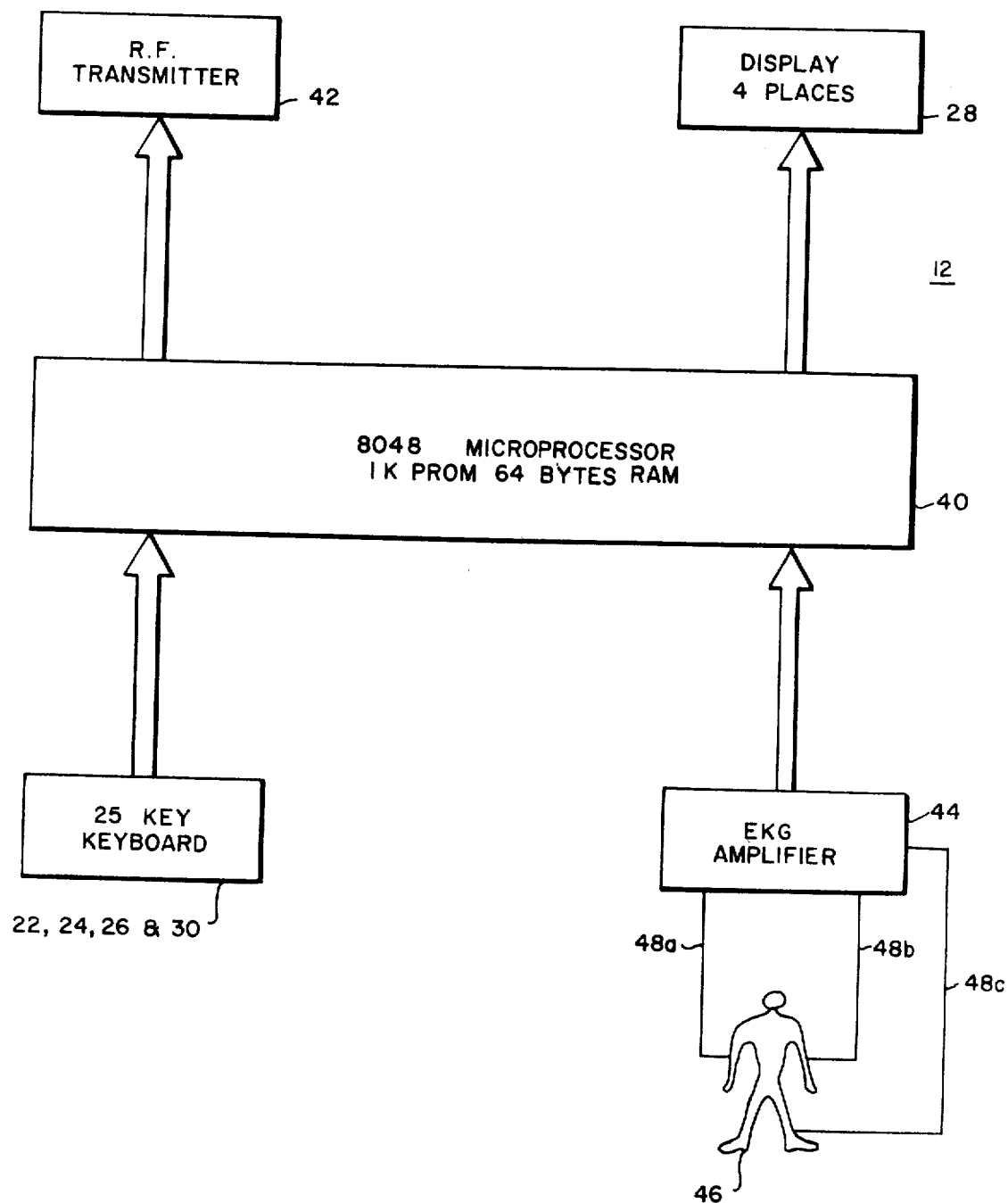

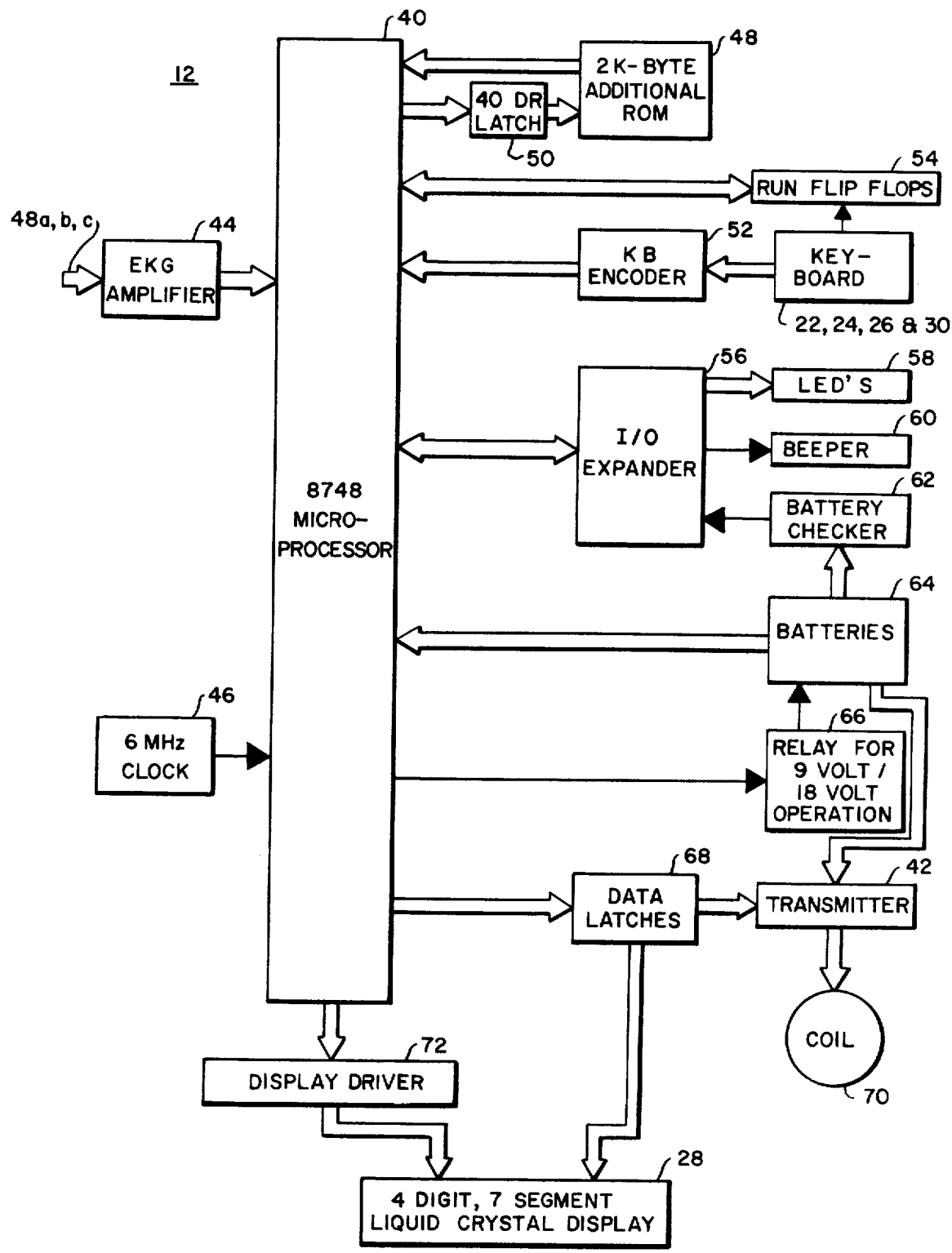

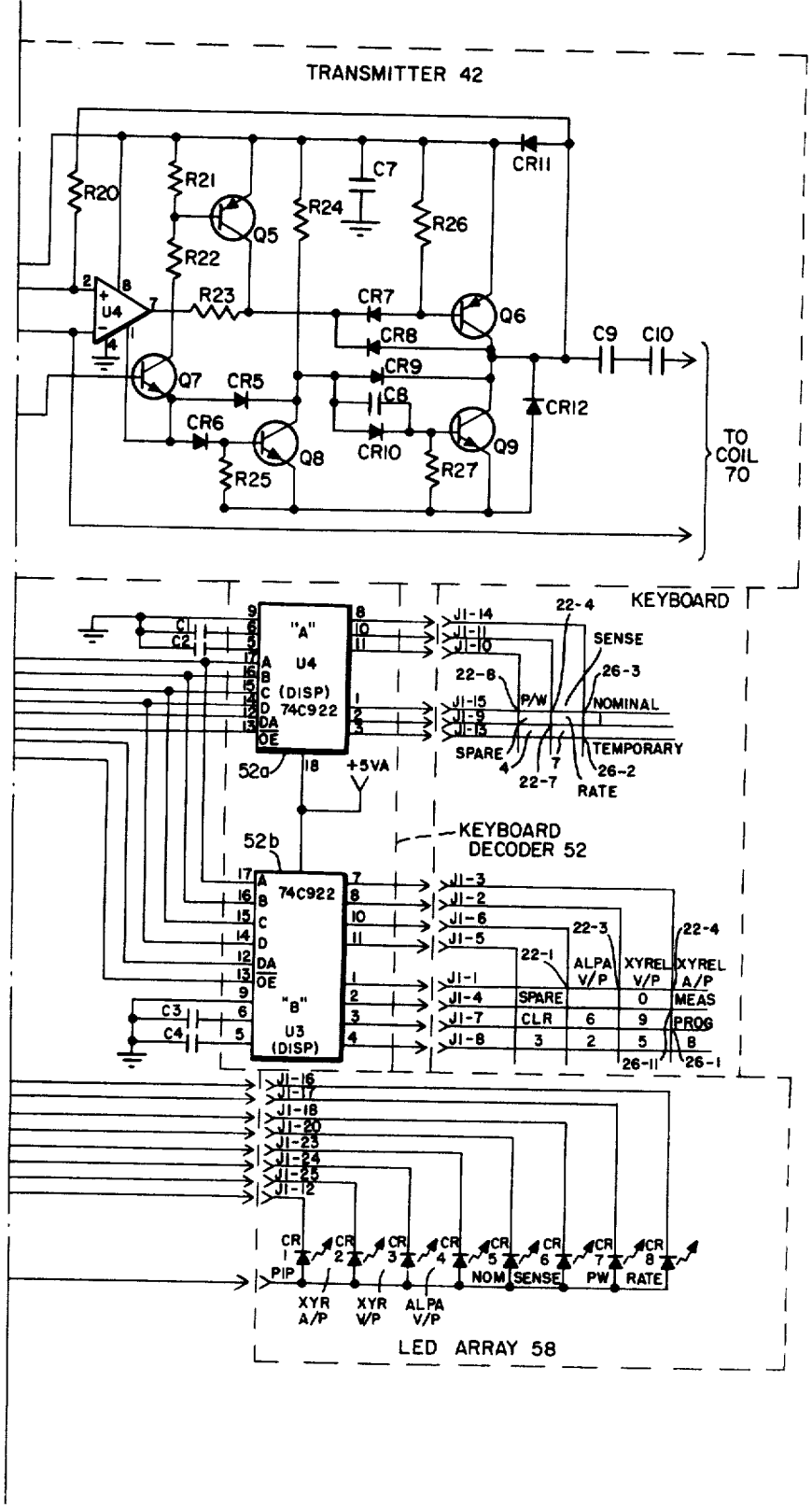

COMPUTER SYSTEM WITH POWER CONTROL CIRCUIT

DESCRIPTION

Cross Reference to Copending Applications

Attention is drawn to the following copending, commonly assigned applications, all each incorporated specifically by reference into the specification;

(1) "CARDIAC PACEMAKER HAVING A RATE LIMIT", by David L. Thompson, Ray. S. McDonald and Yan Sang Lee, filed on Nov. 6, 1978, Ser. No. 957,828;

(2) "DEMAND CARDIAC PACEMAKER HAVING REDUCED POLARITY DISPARITY" by Jerome T. Hartlaub and Ray S. McDonald, filed on Nov. 6, 1978, Ser. No. 957,812, now abandoned;

(3) "DIGITAL CARDIAC PACEMAKER" by David L. Thompson, Jerome T. Hartlaub, Ray S. McDonald and Martin A. Rossing, filed on Nov. 6, 1978, Ser. No. 957,960, now abandoned;

(4) "FREQUENCY TO VOLTAGE CONVERTER FOR CARDIAC TELEMENTRY SYSTEM" by Stanley L. Gruenenwald, filed on Nov. 6, 1978, Ser. No. 958,202, U.S. Pat. No. 4,236,523, issued Dec. 2, 1980;

(5) "SYSTEM FOR DETECTING HEART PACEMAKER PULSES" by Robert McKay Bennett, filed on Nov. 6, 1978, Ser. No. 957,815 U.S. Pat. No. 4,226,245, issued Oct. 7, 1980;

(6) "MULTI-MODE, ADAPTABLE, IMPLANTABLE PACEMAKER" by Stephen R. Duggan, Ser. No. 926,303, filed July 20, 1978, now abandoned and refiled on Mar. 5, 1980 as c-i-p application Ser. No. 127,308; and (7) "PROGRAM TESTING APPARATUS" by Richard M. Powell, and Katherine H. Anderson, Ser. No. 958,064, filed Nov. 6, 1978, U.S. Pat. No. 4,236,524, issued Dec. 2, 1980.

Technical Field

This invention relates to apparatus for programming internally implanted electronic devices adapted to be operated in a variety of programmable modes for stimulating body tissue or to monitor various conditions of the device itself or of body tissue, e.g., the patient's heart.

Background of Prior Art

Heart pacers such as that described in U.S. Pat. No. 3,057,356 issued in the name of Wilson Greatbatch and assigned to the assignee of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectorial region or in the abdominal region of the patient by a surgical procedure, whereby an incision is made in such region and the paceamer with its own internal power supply, is inserted within the patient's body. This pacer operates asynchronously to provide fixed-rate stimulation not automatically changed in accordance with the body's needs, and has proven effective in alleviating the symptoms of complete heart block. An asynchronous pacer, however, has the possible disadvantage of competing with the natural, physiological pacemaker during episodes of normal sinus condition.

An artificial pacer of the demand type has been developed wherein the artificial stimuli are initiated only when required and subsequently can be eliminated when the heart returns to the sinus rhythm. Such a demand pacer is shown in U.S. Pat. No. 3,478,746 issued Nov. 18, 1969 and entitled "CARDIAC IMPLANTABLE DEMAND PACEMAKER". The demand pacer solves the problem arising in asynchronous pacers by inhibiting itself in the presence of ventricular activity (the ventricle's R wave), but by coming "on line" and filling in missed heartbeats in the absence of ventricular activity.

A problem with such prior art, implantable demand pacers it that there was no way to temporarily increase or decrease the rate or other operating parameter at which these stimulating pulses are generated without surgical intervention. Still another problem is the great difficulty in ascertaining a failing electrode, and in establishing an adequate R-wave sensitivity safety margin in an implanted demand pacer.

Another improvement which has occurred since Greatbatch first disclosed the implantable cardiac pacemaker is means to allow the pacemaker to be reprogrammed after it has been implanted. In U.S. Pat. No. 3,805,796 in the name of Reese Terry, Jr. et al, entitled "Implantable Cardiac Pacer Having Adjustable Operating Parameters", which issued in 1974, circuitry is disclosed to allow the rate of the pacemaker to be noninvasively changed after it has been implanted. The rate varies in response to the number of times a magnetically operable reed switch is closed. The Terry et al device operates by counting the number of times the reed switch is closed and storing that count in a binary counter. Each stage of the counter is connected to either engage or bypass one resistor in a serially connected resistor chain, which chain is a part of the RC time constant controlling the pacemaker rate.

The concept of the Terry et al device has been improved upon by the apparatus shown in U.S. Pat. No. 4,066,086 in the name of John M. Adams et al, entitled "Programmable Body Stimulator", which issued in 1978, and which discloses a programmable cardiac pacemaker that responds to the application of radio frequency (RF) pulse bursts while a magnetic field held in close proximity to a magnetically operated reed switch included within the pacemaker package holds the reed switch closed. In the Adams et al circuit, again only the rate is programmable in response to the number of RF pulses bursts applied. The use of radio frequency signals to program cardiac pacemakers was earlier disclosed by Wingrove in the U.S. Pat. No. 3,833,005 entitled "Compared Count Digitally Controlled Pacemaker" which issued in 1974. The Wingrove device was capable of having both the rate and pulse width programmed.

One area where cardiac pacing technology has lagged behind conventional state of electronic technology involves utilization of digital electrical circuits. One reason for this has been the high energy required to operate digital circuits. However, with more recent technology advances in complimentary metal oxide semiconductor (CMOS) devices fabricated on large scale integrated circuits, together with the improvements of cardiac pacemaker batteries, digital electronic circuits are beginning to be utilized in commercial pacemakers. The inherent advantages of digital circuits are their accuracy, and reliability. Typically, the digital circuit is operated in response to a crystal oscillator which provides a very stable frequency over extended periods of time. There have been suggestions in the prior art for utilizing digital techniques in cardiac stimulators and pacemakers since at least 1966. For instance, see the article by Leo F. Walsh and Emil Moore, entitled "Digital Timing Unit for Programming Biological Stimulators" in *The American Journal of Medical Electronics*, First Quarter, 1977, pages 29 through 34. The first patent suggesting digital techniques is U.S. Pat. No. 3,557,796 in the name of John W. Keller, Jr., et al, and is entitled "Digital Counter Driven Pacer", which issued in 1971. This patent discloses an oscillator driving a binary counter. When the counter reaches a certain count, a signal is provided which causes a cardiac stimulator pulse to be provided. At the same time the counter is reset and again begins counting the oscillator pulses. Additionally, in the Keller et al patent, there is disclosed the digital demand concept, in which the counter is reset upon the sensing of a natural heartbeat, and the digital refractory concept, in which the output is inhibited for any certain time after the provision of a cardiac stimulating pulse or the sensing of a natural beat.

As mentioned above, digital programming techniques are shown in both the Terry et al U.S. Pat. No. 3,805,796 and the Wingrove U.S. Pat. No. 3,833,005. Wingrove additionally discloses digital control circuitry for controlling the rate of the stimulating pulses by providing a resettable counter to continually count up to a certain value that is compared against a value programmed into a storage register. The Wingrove patent also shows provisions for adjusting the output pulse width by switching the resistance in the RC circuit which controls the pulse width.

Though there has been suggested that various parameters, i.e., pulse width and rate, may be changed within an internally implanted pacer, it is desired to provide a device that is capable of operating in various, different pacing and/or sensing modes. The systems of the prior art are capable of storing by means of digital counter circuitry a programmable word indicative of desired rate or pulse width. In an internally implanted device, the space to incorporate a plurality of such counters whereby a number of such functions could be programmed, is indeed limited.

In FIG. 1, there is shown an universally programmable pacemaker system 10', which includes a programmer 12, a programming head 14, and an implantable pacemaker 16. Signals generated by the pacemaker 16 are applied through leads 18 to the heart (not shown) to cause the contraction thereof. The type of signals applied from pacemaker 16 through leads 18, as well as the response of the heart to these signals, is well known in the art and will not be discussed herein.

In the above-identified application entitled "Digital Cardiac Pacemaker", there is described a programmable pacemaker such as pacemaker 16 which includes means adapted to provide electrical stimulation signals to at least one lead for stimulating body tissue and sensing means for detecting the natural currents of electrical activity of the patient's heart and in response to such electrical activity including the patient's ECG and pacer pulses, generates and transmits corresponding electrical signals. As described in detail in the noted application, the pacemaker 16 includes a program storage means for accepting and storing program signals to influence the electrical stimulation circuitry and the sensing circuitry. The programmer 12' is designed to transmit coded signals to such a pacing generator illustrated in FIG. 1 as element 16 to effect changes of the mode and the parameters of the stimulating mode effected upon the patient, as well as to change the manner of sensing the electrical activity of the patient's heart. The keyboard is made up of a switching array to provide a plurality of switches or switching points, whereby different parameters and modes of operation may be programmed.

Illustratively, it is desirable to be able to program the sensitivity of the sense amplifier included within the pacemaker 16 so that it can more or less be sensitive depending on the patient's needs. In addition, it is desirable to be able to program the refractory period of the pacemaker 16, which is not readily apparent from viewing the EKG. Further, it is desirable to be able to program the stimulating rate, the width of the pacer pulses; the amplitude of the stimulating pulses; in a hysteresis mode of operation, the percentage less of the rate of which the pacing generator will initiate its stimulation from the limit to be detected to initiate such pacing; and a set of nominal values of these parameters at which if the operator elects, to return the operation of the pacing generator in an emergency situation. In addition, the pacemaker 16 may be programmed in a variety of modes of operation including a demand mode of operation, a synchronous operation in which the pacemaker pacing generator is made to generate pacing pulses synchronous with the detecting of the patient's R wave, asynchronous mode in which the pacing generator applies stimulating pulses at a fixed rate, an inhibit mode of operation in which the programmed operation of the pacing generator is inhibited so that the physician may observe the normal contracting of the patient's heart without the aid of the pacing generator, a measure mode of operation in which the patient's heart activity including his EKG and pacing pulses are meaasured and displayed, a temporary mode of operation in which a desired set of parameters are adopted for a test period and an auto-threshold mode of operation in which the pulse width of the pacing pulse applied to the patient's heart is incrementally decreased until the pacing pulses are no longer able to stimulate the patient's heart, i.e., heart capture is lost. It is noted that it is not only necessary to be able to transmit coded messages to the pacemaker 16, which may be implanted as noted above in the patient, but also to receive and to monitor the effect of the changing of these parameters by the display of the patient's heart activity. The pacemaker 16 described in the above-identified application entitled "Digital Cardiac Pacemaker," is capable of checking whether the parameter or mode of operation sought to be programmed has been actually entered into the storage means of the pacing generator. Further, provision must be made to prevent operator error so that inappropriate parameters or modes of operation may not be entered into at inappropriate times.

In the above-identified application entitled "PROGRAM TESTING APPARATUS," there is described in detail the programmer 12' for transmitting encoded signals to the pacemaker 16 to effect the programming of a mode and/or parameter of the pacemaker's operation. The programmer 12' includes electrodes coupled to the patient's body for sensing his heart activity signals including the stimulating pulses, a keyboard for entering a parameter and/or mode od operation to be programmed within the pacemaker 16, a transmitter for encoding and transmitting the parameter, and/or mode of operation to the pacing generator, and a measuring circuit for measuring the characteristics of the detected heart activity and the artifacts generated by the pacemaker 16 to provide a manifestation of the patient's heart activity and a manifestation that the pacemaker 16 has been successfully programmed. The programmer 12' includes a display for providing the manifestations to the operator of the successful programming of the pacing generator.

The programmer 12 as described in the above-identified application entitled "PROGRAM TESTING APPARATUS" was designed to program a wide variety of parameters and modes of operation, and was energized through AC outlets as would be typically found in a hospital or a Doctor's office. By contrast, the subject invention is directed toward a portable, battery-powered programmer for the pacemaker 16, as described in the above-identified patent application entitled "DIGITAL CARDIAC PACEMAKER". As indicated above, there has been a hesitancy to incorporate digital devices including micro-processors into pacemakers or any battery operated device such as the contemplated programmer, due to the high power requirements of such components. This problem is further compounded when it is realized that the encoded signals are transmitted by RF transmission to the internally implanted pacemaker, the transmitter of the programmer requiring even higher power for operation than normally would be contemplated for the other, digital components of the programmer.

SUMMARY OF THE INVENTION

In accordance with this invention, there is described a digital computer system comprising an input data circuit, a processor for executing a program stored in a memory to process the inputted data, a depletable energy source (e.g. a battery) for energizing the elements of the computer system, and a power control circuit for selectively controlling the drain imposed upon the energy source in accordance with the data input into the system and the program executed by the processor. In an illustrative embodiment of this invention, the power control circuit is operative in at least three modes of operation, namely off/rest, power down, and operating. In the off/rest mode, the power control circuit energizes a storage element illustratively taking the form of a flip/flop to be receptive to an initialization signal as derived from an on/off switch to dispose the power control system from its off/rest mode to its power down mode. The storage element is energized throughout the entire operation of the system including the off/rest mode, wherein the remaining elements of the computer system are denergized. In the power down mode, the control circuit applies power to the data input means. In an illustrative embodiment of this invention, the data input means includes a key board and a decoder for providing a signal indicative that one of the keys has been depressed. Upon actuation of the key, a data available signal DA is transmitted to the power control circuit, whereby the computer system is disposed in its operating mode, wherein all of the elements of the computer system are energized. In its operating mode, the processor and its memory are fully energized to execute the stored program.

In a further aspect of this invention, certain conditions will occur during the execution of the program that will require the power control circuit to dispose the system from its operating mode either to its power down mode or off/rest mode dependent upon the state of the computer system or the step being executed. Illustratively, the process is adapted to check various conditions of the computer system e.g., the operability of the contacts of the key board, and the voltage level of the battery source. If the battery voltage is below a predetermined level at which the computer system may no longer operate, a signal is applied to the power control circuit, whereby the system is disposed from its operating mode to its off/rest mode. Similarly, if the key board is malfunctioning, the power control circuit will dispose the system to its off/rest mode. Further, the program is designed to permit data entry by actuation of the key board in a given sequence. When a key is depressed, that key is identified and it is compared with the known sequence be stored within the truth table of the system's memory, and if not within the desired sequence, the system directs the control circuit to transfer from the operating to the power down mode. In such a power down mode, the system pauses to wait for the next actuation of the data input means, while imposing a minimum power drain upon the battery and extending its life.

In an illustrative embodiment of this invention, the computer system is particularly adapted to be used to implement a programmer for programming the functions, parameters and values of the parameters of a pacemaker as would be used to stimulate a patient's heart. The contemplated programmer comprises a key board by which each of the functions to be performed by the pacemaker, the parameter to be programmed for example rate or pulse width of the stimulating pulses of the pacemaker, and the value of the selected parameter may be programmed. The programmer further includes a transmitter for encoding and transmitting via radio waves the encoded signals to the pacemaker, whereby they may be stored within the pacemaker's memory to effect its operation. The adapted computer system as described above, includes a further fourth mode of operation wherein the system is adapted to go to a transmitting or program mode of operation, whereby an energizing signal of increased voltage is applied to the transmitter during its transmitting operation. To this end, the key board includes a program key which upon being actuated, controls the power control circuit to develop the energizing signal of higher voltage level. Illustratively, the power source may include first and second batteries and a switch means that is disposable from a first or normal position wherein the first and second batteries are connected in a parallel configuration, to a second position to connect the batteries in a series configuration to provide the energizing signal of increased level. In particular, when the switch is disposed to a second position, the programmer/computer system is disposed to its transmitting mode, whereby the energizing signal of increased level is provided to the system's transmitter to transmit the encoded signal to the pacemaker.

In a further aspect of this invention, the programmer as implemented by the computer system of this invention includes an EKG shaping and amplifying circuit coupled by electrodes to various portions of the patient's body, whereby the artifact signals as generated by the implanted pacemaker are sensed and applied by the shaping and amplifying circuit to the processor of the computer system and in particular, to its interrupt input. The key board includes a measure key which upon actuation enables the interrupt input of the processor to receive the artifact signals. The processor detects first and second, successive pacer artifact pulses to actuate a first counter to count pulses for that interval between the first and second pulses and to initiate a second counter to measure the pulse width of at least one of the pulses. In an illustrative embodiment of this invention, the first such pulse initiates the first counter within the microprocessor and the second pulse terminates the counting of the first counter to provide an indication of interval therebetween and thus the pulse rate of the pacing pulses. The second counter is initiated to count upon the occurrence of the leading edge of the second pulse and terminates counting upon the sensing of the trailing edge of the second pulse to thereby provide an indication of pulse width.

BRIEF DESCRIPTION OF THE DRAWINGS

The advantages of the present invention will become more apparent by referring to the following detailed description and accompanying drawings, in which:

FIG. 1 shows the entire system including a programmer and monitoring device in accordance with the subject invention and an implantable pacing generator to be programmed by the programmer;

FIG. 2 shows the key board arrangement whereby various modes of operation may be entered into and various parameters set by the programmer of this invention into the pacing generator;

FIG. 3 shows the wave form of the signal to be transmitted from the programmer of the subject invention to the programmable pacemaker;

FIG. 4 shows in block format, one programming word and the various portions thereof;

FIGS. 5 and 6 are respectively a general and a more detailed block diagram of the configuration of the elements forming the computer system of the programmer of this invention;

FIGS. 8A to 8L (no FIGS. 8H and 8I) show in flow diagram form, the steps of the control functions to be implemented by the programmer of this invention to effect an entry of parameters within the pacing generator and to effect a shift of the mode or energized state of the various elements of this system as shown in FIGS. 5, 6 and 7.

DESCRIPTION OF THE PREFERRED EMBODIMENTS

Figure 7A:
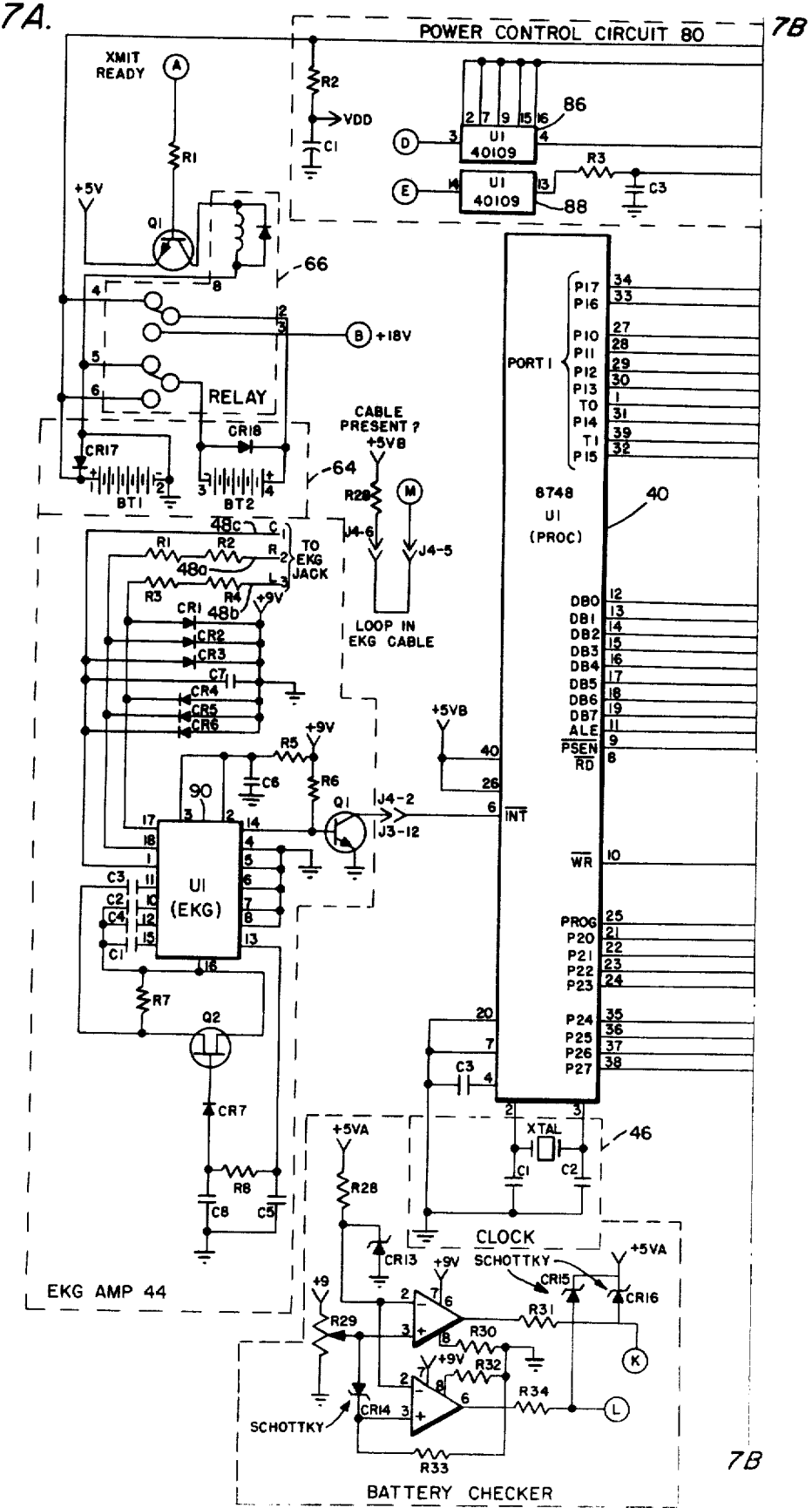
FIGS. 7A, B and C are a detailed circuit diagram of the computer system forming the programmer as generally shown in FIGS. 5 and 6.

The entire programmable pacemaker system 10 contemplated by this invention is similar to that shown in FIG. 1, noting that the programmer 12 of this invention is adapted to program the same implantable pacemaker 16 as described in the above-identified patent application entitled "DIGITAL CARDIAC PACEMAKER." As shown in FIG. 2 the programmer 12 of this invention includes a key board whereby various functions, parameters and the values of the parameters to be programmed may be entered upon the keys 22, 26 and 24, respectively. In addition, a display 28 is included so that the operator can view a wide variety of information including manifestations that an error in the programming has occurred, or confirmation that the entered parameters or change of mode of operation has indeed taken place. After a mode of parameter has been selected and the corresponding value of the parameter entered, the program key 26-1 is actuated to transmit a series of radio frequency burst signals from the programmer 12 through the connector 30 to the head 14, to be detected by a receiver within the programmable pacemaker 16. The head 14 includes a permanent magnet of sufficient size to cause a magnetically actual reed switch (not shown) within the pacemaker 16 to be closed. A detailed description of the reed switch, its operation and connection through remaining circuitry of the pacemaker 16, is found in the above-identified application, entitled "DIGITAL CARDIAC PACEMAKER." The closure of the reed switch in the pacemaker 16 allows circuitry within the pacemaker 16 to detect and process RF signals applied over the conductor 30 to head 14. As will be explained in detail later, the programmer 12 includes a radio frequency (RF) burst signal transmitter which is designed to provide a train of radio frequency signals of the type herein after described with respect to FIGS. 3 and 4.

As will be explained in detail later, a portion of the programmer's circuitry always remains energized to sense the actuation of the on/off key 22-2. When the on/off key is pressed, a short e.g., 2 second, self-diagnostic sequence or process will be effected whereby various portions of the programmer 12 are tested. First, each segment of the display 28 is turned on, followed by a short beep emanating from an audio transducer within the programmer 12. Also, each of the keys 22, 24 and 26 will be scanned to make sure that no keys have failed with the contacts closed. The battery voltage is then checked to determine whether it is within acceptable limits. If all functions are not functional, the display 28 will flash with all "9999" and the audio transducer will beep three times. Otherwise, if all functions are operating normally, the programmer 12 will display all "0000" on its display 28 and power down its processor (to be later described), while leaving the remaining portions of it's circuitry energized. Next, one of the parameter keys 22-4, 22-3, and 22-1, which designate specific models of pacemakers as manufactured by the assignee of this invention, is actuated to initiate the programming of that pacemaker. Thereafter the portion of the key board that has been depressed will be back lighted by a light source illustratively in the form of a light-emitting-diode (LED). After designating the particular model of the pacemaker 16 to be programmed, a key identifying the particular parameter, to be programmed is depressed. The parameter keys include keys for programming the rate and pulse width of the cardiac stimulating pulse, the sensitivity of the pacemaker's sensing amplifier, and the mode. For example, the operator may depress the RATE key G22-7 to program the rate in which the stimulating pulses are to be applied by the pacemaker 16 to the patient's heart. Thereafter, the operator enters via the numeric keys 24 a selected value of the rate to cause the programmer 16 to generate signals indicative the particular value of that parameter. In order to minimize the drain placed upon the power source of the programmer 12, e.g. two batteries as will be described, a timing period in the order of 15 seconds is set upon the actuation of any of the RATE key 22-7, the PW key 22-7 or the SENSE key 22-9. The numeric value of the selected parameter may be entered within that period, otherwise, the programmer 12 will turn itself off after the 15 second interval has timed out. Any time a wrong sequence of keys is pressed, for example a value of a parameter is entered that cannot be accepted by the pacemaker 16, an appropriate error manifestation is indicated by flashing all "999" on the display 28. In an illustrative embodiment of this invention, only the following values of the parameters rate, pulse width, sensitivity, XYREL TM VP Rate, and SPECTRAX TM VP Rate, and XYREL TM AP Rate may be programmed;

TABLE 1

| Allowable Parameter Values | |
|---|---|
| SPECTRAX<sup>TM</sup> VP RATE: | 30 to 150 bpm at 5 bpm intervals (Above 130 bpm to 150 bpm unit must be in temporary mode only) (25 rates) |
| PULSE WIDTH: | .1, .3, .5, .8, 1.6ms (5 PWs) |
| SENSITIVITY: | 1.25, 2.5, 5.0 mv (3 Sen's) |
| XYREL<sup>TM</sup> VP RATE: | 30, 50, 60, 70, 75, 80, 90, 100 bpm |
| XYREL<sup>TM</sup> AP RATE: | 30, 60, 70, 80, 90, 100, 115, 130 bpm |

As each of the numerical keys 24 is depressed, that number appears upon the display 28 at the appropriate location. Further, as each of the RATE key 22-7, the PW (pulse width) key 22-8, the SENSE (sensitivity) key 22-9, the NMNL (nominal) key 26-3, or the MEAS key 26-11 is depressed, a single beep is heard from the audio transducer and a backup LED is turned on to eluminate the particular key that was depressed.

The pulse width of the pacing pulse is designated to be programmed by pressing first the PW button 22-8, before entering via the numeric keys 24 the particular value of pulse width to be programmed.

The SENSE push button 22-9 is pushed to initiate a change within the sensitivity of a sensing amplifier within the pacemaker 16, whereby the gain or sensitivity of, that amplifier that amplifies the R wave signals of the patient may be changed dependent upon the individual patient, his condition and the connection of the pacing generator leads to the patient's heart. In this manner, the R wave signals, as well as the detected pacing pulses, may be amplified without saturation to be used by the pacing generator in various modes of operation.

The operator may effect a temporary mode of operation by depressing the TEMP push button 26-2, in order to enter a test mode of operation. After a pacemaker has been implanted and programmed to one mode and one set of parameters, the physician may periodically want to check the patient and see how his response is to the programmed mode and parameters. For instance, the physician may desire to change the rate at which the pacemaker 16 is applying pulses or he may wish to change the pulse width, in a manner as described above. During the time the physician is checking the pacer 16 by changing the operating parameters and values, he may wish to compare the new results achieved with the original results. After comparison he may determine that the original parameters are preferable or he may determine that the new parameters should be programmed into the pacer. In order to allow this, it is desirable that the pacing generator 16 be able to be temporarily programmed to new parameters and then if the new parameters are not to be permanently maintained, the original parameters be automatically restored. Such a temporary mode can be accomplished by temporarily programming the pacing generator 16, by pressing the TEMP button 26-2. The pacemaker 16 as described in the above-identified application, entitled "Digital Cardiac Pacemaker", includes detecting means responsive to an applied coded programming signal indicative of the temporary mode, a memory for storing a code relating to the code of programming signal whenever the programming signal manifests that the operating parameter of the pulse generator are to be permanently changed with the memory means providing a parameter defining signal related to the code stored thereby, and a generator signal providing means responsive to the parameter defining signals for providing cardiac stimulating signals according to the desired operating parameters. The detecting means indicates that at least one set of operating parameters is to be temporarily programmed during a determinable time, and provides during that determinable time, temporary parameter defining signals to the signal providing means in place of the parameter defining signals provided from the memory, and for providing the permanent parameter defining signals to this signal providing means after the determinable time. The pacing generator 16 will retain the temporary parameters until either: (a) a new permanent or temporary value is programmed, or (b) the programmer 12 is turned off or programmer head 14 is withdrawn.

The operator may depress the CLEAR button 24, when the operator senses that an error has been made in the entry of a change of a parameter or mode of operation, whereby the programmer 12 returns to an initial point in the programming procedure and the mistakenly entered signals are erased.

If the operator senses by observing the display 28 that the patient's heart is not pacing properly either naturally or artificially, the operator may depress the NMNL (nominal) key 26-3, causing the programmer 12 to automatically transmit a set of encoded signals stored in the programmer 12 whereby the nominal parameters, including rate, pulse width, sensitivity, amplitude output of the pacing pulse, the refractory period, hysteresis and demand mode, are stored within memory of the pacing generator 16. As described in the above-identified application entitled "Digital Cardiac Pacemaker", the pacing generator 16 includes a storage or memory circuit for receiving such encoded signals for effecting a corresponding type of pacing.

After a set of parameters and mode of operation have been entered via the appropriate keys and a check has been made to see whether the entered parameters or mode are within defined limits, to be discussed, the programmer user depresses the PROGRAM push button 26-1, whereby these encoded signals are transmitted via the programming head 14, whereby corresponding signals are induced within a coil within the pacing generator 16 and subsequently stored within the generator's memory.

If the MEAS (measure) key 26-11 is pressed, a check is made to determine if the leads coupled from the programmer 12 to the patient's body are connected and if so, an LED disposed behind the RATE key 22-7 is first energized and thereafter the measured value of the rate of the patient's EKG is displayed upon the display 28 for a given period of time e.g., 2 to 3 seconds. Thereafter, the LED disposed behind the PW key 22-8 is turned on, and the measured pulse width is displayed upon display 28 for a like period of time. After this sequence, the circuitry of the programmer 12 is turned off to conserve the drain upon its batteries.

Referring now to FIGS. 3 and 4, the type of data generated by programmer 12 will be described. Each different programming operation requires the transmission by programmer 12 of a thirty-two binary digit (bit) word with each bit being either a logic "1" or a logic "0" binary number. The actual signals generated by programmer 12 are bursts of radio frequency signals at a frequency of approximately 175 kilohertz. For each word to be generated by programmer 12, thirty-three virtually identical RF bursts are applied. Each bit is in turn defined by the real time separation between successive RF bursts. In the preferred embodiment described herein a relatively long time will be defined as a logic "1" bit and a relatively short time will be defined as a logic "0" bit. The pulse burst duration may be approximately 0.35 msec, the relatively long time may be approximately 2.1 msec and the relatively short time may be approximately 0.7 msec. Thus, for example, as shown in FIG. 3, an arbitrary series of nine RF bursts are shown in the upper graph. These nine bursts have been processed into pulses by RF demodulation circuitry within pulse generator 16 and are seen as a series of pulses in the lower graph of FIG. 3. Beneath the lower graph of FIG. 3 is a series of eight binary numbers placed at the beginning of each of the second through ninth pulses. Each of these numbers represent the bit manifested by the duration between that pulse burst and the one preceding it. Thus, for the signal shown in the upper graph of FIG. 3, the binary code would be "10010100". This binary number can be written in an octal number system as "224" in a conventional manner. The first number of the octal number represents the first two most significant bits. The middle number of the octal number represents the next three bits and the last number of the octal number represents the last three least significant bits. Hereafter for convenience, all programming codes will be manifested in the octal number system.

Referring to FIG. 4, an illustrative example of the thirty-two bit words generated and transmitted by programmer 12 to pulse generator 16 will be described. The thirty-two bit words consist of four parts, each of which is eight bits in length. These four parts are parameter code, data code, access code and parity code and are generated in that order, the least significant bit first. The first three bits of the eight bit parameter code are not used whatsoever and are always generated as logic "0" bits. The fourth bit of the parameter code is either a logic "1" or a logic "0" bit, which respectively manifests either a temporary or permanent programming command and the last four of the parameter bits represents the code for the particular one of the function keys 26 depressed by the operator in operating programmer 12.

The data code portion of the programming word consists of eight bits which define a particular value for the parameter selected.

Following the data portion of the programming word is the eight bit access word which always consists of the octal code "227". This word is utilized to start the process of programming the pulse generator 16. One purpose for the access word is to prevent extraneous signals which may be detected by pulse generator 16 from causing a reprogramming.

The final eight bit portion of the programming words consists of an eight bit parity code which is generated to provide proper vertical parity based on the parameter and data portions of the word. Again the parity portion is used as a check to prevent extraneous or undesirable programming of pulse generator 16.

The parameter portion of the DATA signal defines one of the parameters to be modified and whether that modification is to be in a temporary or permanent manner, if that choice is available. The illustrative parameters or modes of operation are PW (pulse width) (key 22-8), RATE (key 22-7), NMNL (nominal) (key 26-3), SENSE (sensitivity) (key 22-9), temporary mode (26-2), and MEAS (measure) (26-11). Of the above parameters, the XYREL TM rate, and nominal can not be done in a temporary mode. As will be described hereafter in more detail, the temporary mode of programming causes pulse generator 16 to be programmed for as long as head 14 is positioned over pulse generator 16, which maintains a reed switch (not shown) within the pacemaker 16 closed or until another programming word is provided. Upon the opening of the reed switch or the transmission of another programming word, the original conditions programmed into pulse generator 16 will again control unless, of course, the new programming word modifies that condition.

Each time the transmitter within the programmer 12 transmits a coded signal as described with respect to FIGS. 3 and 4, a determination is made of whether the memory within the pacemaker 16 has in fact, been successfully programmed. As described in the above-identified application entitled "Digital Cardiac Pacemaker", there is included within the circuitry for generating the stimulating pulses, a detection circuit for recognizing the successful programming of its memory by the transmitted, encoded signal. If successfully transmitted and programmed, the pacing circuitry is caused to generate a "PIP" pulse of a selected pulse width in the range between 350 micro-seconds and 1.1 miliseconds and transmitted within a "PIP" interval after generation of the pacemaker's stimulating pulse in the range from 50 and 150 msec. Thus, a check is made by the programmer 12 to detect first the generation of the pacemaker's pulse and thereafter to look for the "PIP" pulse to determine whether the corresponding parameter or mode has been successfully entered. Briefly, this checking process measures the interval between the pacing pulse and the PIP pulse and determining whether that interval falls within the predetermined PIP interval. If the PIP pulse is so detected, an LED disposed behind the PIP space 30 will be illuminated for a given interval of 2 to 3 seconds to thus indicate that the pacemaker 16 has been successfully programmed.

Referring now to FIG. 5, there is shown in an overview of the architecture of the elements comprising the programmer 12. As indicated in FIG. 2, the programmer 12 includes a key board made up of the keys 22, 24, 26 and 30, whereby inputs indicative of the desired function, parameter and value of the selected parameter are entered into a microprocessor 40 illustratively taking the form of that microprocessor manufactured by INTEL CORPORATION under their designation 8748. In addition, the artifact pulses, as well as the "PIP" pulses as generated by the pacemaker 16, are detected by electrodes connected to a patient 46 and transmitted via coupling leads 48a, 48b, and 48c from respectively the right arm, the left arm and the left leg of the patient 46, via an EKG amplifier to the microprocessor 40. After the desired mode of operation and/or value of the parameter have been entered via the key board, the microprocessor 40 commands the transmitter 42 to transmit the encoded signals to the pacemaker 16. In addition, various manifestations of the process effected by the microprocessor 40 including error in the selection of the keys, the measured indication of pulse width and rate of the pacemaker's, the pulses entered parameter, etc, are displayed upon the display 28.

The frequency demodulator incorporated within the transmitter 42 is more fully described in the above referenced application entitled "FREQUENCY TO VOLTAGE CONVERTER FOR CARDIAC TELEMETRY SYSTEM."

Referring now to FIG. 6 there is shown a more detailed schematic block diagram of the system comprising the programmer 12. As further shown, a system clock 46 is coupled to the microprocessor 40, which is coupled by an encoder 52 to the keyboard comprised of the keys 22, 24, 26 and 30. As indicated above, selected of these keys are backlit upon actuation, by a corresponding LED 58 disposed in an array to align the LED's with the keys. The corresponding LED is energized via signals directed from the microprocessor 40 through an I/O expander 56. In addition, the I/O expander 56 additionally energizes a beeper 60 to either indicate as by a short, single beep the successful actuation of a key of the key board, or a series of beeps to indicate an error on the entry of data via the keyboard. Further, a battery checker 56 is coupled to the batteries 64 to provide an indication of the status of the batteries 64. As indicated in FIG. 6, the batteries 64 are directly connected to the microprocessor 40 and to the transmitter 42, whereby the elements of the system are appropriately energized. In an illustrative embodiment of this invention, there are two batteries for energizing the system comprising the programmer 12. The batteries may be connected in a first series configuration, whereby the output obtained therefrom is of a relatively high voltage level e.g., 18 volts, or in a second, parallel configuration whereby a lower, 9 volt output is obtained. The switching between the first series and second parallel configuration is effected by relay 66 as controlled by an output derived from the miroprocessor 40. Upon the successful programming of a parameter or function in the actuation of the program key 26-1, the signals are encoded and transmitted by the microprocessor 40 via a data latch 68 to the transmitter 42, whereby RF signals are transmitted via a coil or antenna 70 to the pacemaker 16 as typically implanted in the patient. In addition, data is stored in data latches 68 to be displayed by the display 28 which illustratively takes the form of a four digit, 7 segment liquid crystal display, as energized by a display driver 72.

Referring now to FIGS. 7A, B and C, there is shown a detailed schematic of the system comprising the programmer 12, wherein the detailed circuit elements as generally identified in FIG. 6 are encircled by dotted lines and identified by like numerals. For example, the circuit comprising a battery checker is identified by the numeral 62. A +5 volts as produced by the first and second batteries BT1 and BT2 is applied to the battery checker 62. Further, the clock 46 is comprised essentially of a crystal oscillator, which produces and applies its 6 MHz clock signal to the microprocessor 40. Further, actuating signals are applied from the micropressor 40 to the display driver 72 whereby data stored in the latch 68a may be selectively displayed upon the LCD display 28. The keyboard is illustrated as comprising two arrays of interconnecting X and Y coordinate conductors, each spaced from the other in order to form an array of keys as shown in FIG. 7C. Each array of conductors is coupled to its own keyboard decoder 52a or b, whereby the coded signals are applied to corresponding inputs of the miroprocessor 40. As will be explained, each of the decoders 52a or b may be separately energized depending upon which of the arrays of conductors is depressed to minimize the energy required by the system. The output P73 of the I/O expander 56 is coupled to energize the beeper 60. In addition, the P42-53 outputs of the I/O expander 56 are connected to the array 58 of LEDs, whereby upon actuation of one of the keys of the keyboard, a corresponding LED is energized to light up a particular portion of the keyboard comprised of a transparent face plate with corresponding identifying numerals, as shown by FIG. 2.

The encoded data in the format as shown in the FIGS. 3 and 4 is derived from the P16 output terminal of the microprocessor 40 and is applied via the "DATA" conductor to the transmitter 42, along with a "READY" signal of increased voltage, e.g., 18 volts, energizing the transmitter 42 to transmit the encoded signal. In this regard, it is noted that the system as depicted in FIGS. 7A, B and C is operated in at least two modes or voltage levels, a low level illustratively in the order of 9 volts, and a high level illustratively in the order of 18 volts. The transmitter 42 requires the higher voltage level to operate during the transmission of the encoded signal via the coupled coil 70 to the pacemaker 16. During those times of transmission, the "READY" signal is generated from the P17 terminal of the microprocessor 40 and is applied through transition point A to the base of transistor Q1, whereby the energizing coil of the relay 66 is energized to throw the switches from the position as shown in FIG. 7A to the other position, whereby the batteries BT1 and BT2 normally connected in parallel are now connected in a series configuration to provide a high level voltage via terminal P18 to the transmitter 42. In this manner, during those relatively short periods in which the transmitter 42 is operative to transmit its encoded signal, the higher level voltage is provided by connecting the batteries BT1 and BT2 in a series configuration, thus minimizing the drain that otherwise would be imposed by the transmitter 42 if it was continuously connected to the series connected batteries BT1 and BT2.

Figure 7B:
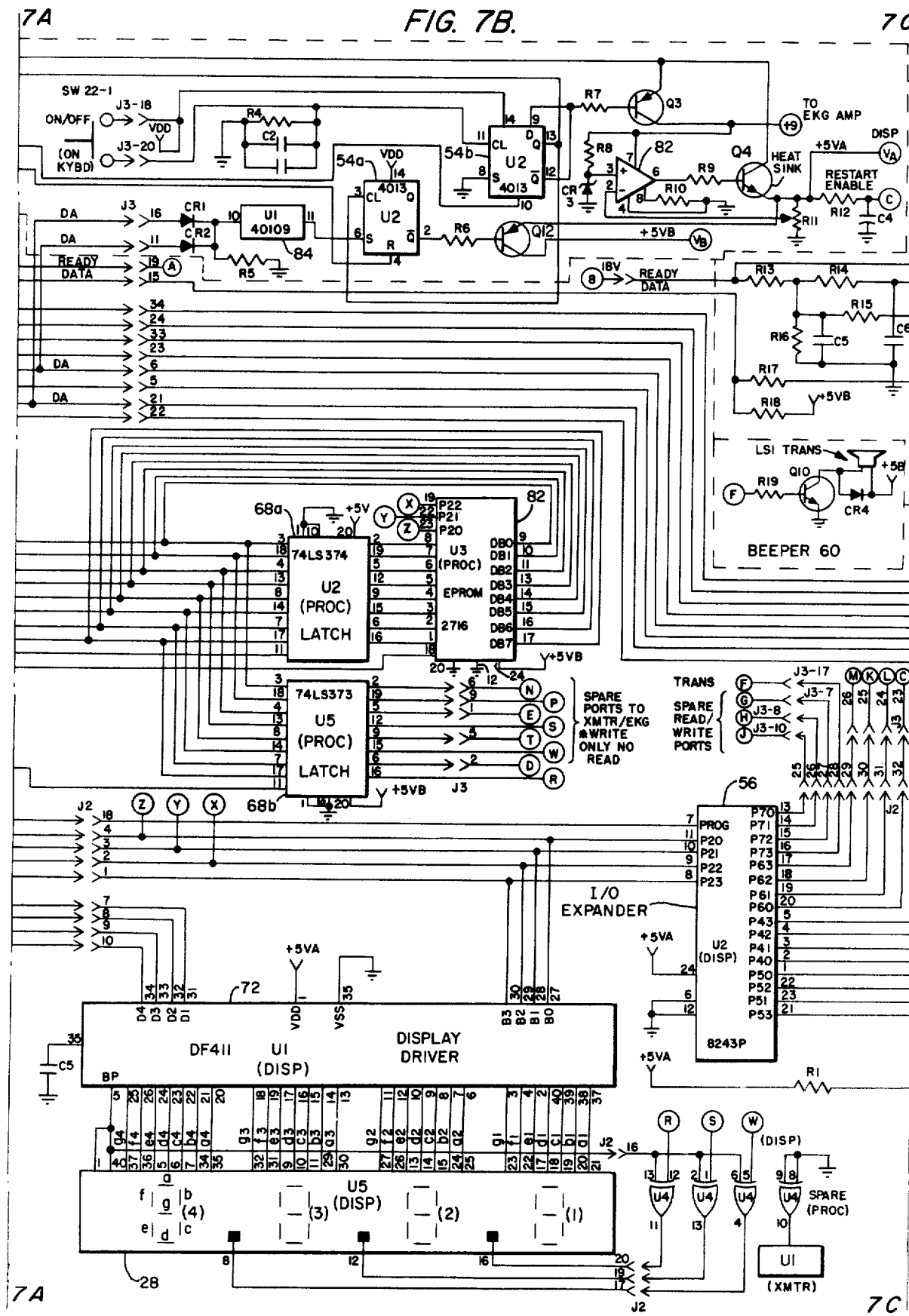

In addition to the transmit state, the battery energized computer system as illustrated in FIGS. 7A, B and C may be operated in the following, three additional modes: (1) OFF/REST, (2) Power Down, and (3) Operating. Initially, before the system of FIG. 7 is turned on by depressing the on/off switch 22-1 (shown in FIG. 2 as being part of the keyboard, but shown in FIG. 7C as being within the power control circuit 80), the system is in its Off/Rest mode wherein only a power down flip/flop 54a and a master flip/flop 54b are energized. As seen in FIG. 7A, the batteries BT1 and BT2 are normally connected by the relay 66 in parallel with each other whereby a low level voltage, e.g., 9 volts is applied to the midpoint between resistor R2 and capacitor C1, to provide a supply voltage $V_{DD}$ to energize continuously the flip/flops 54a and 54b. In this regard, the remaining components of the system of FIGS. 7A, B and C are not energized in that the further supply voltages as provided by the power control circuit 80 are deactuated. Upon closing of the on/off switch 22-1, a highgoing signal is applied to the clock input of the master flip/flop 54b whereby its Q output goes high, rendering transistor Q3 conductive to provide a voltage signal in the order of 9 volts to the EKG amplifier 44. As shown in FIG. 7A, the 9 volts are applied to various energization points of the EKG amplifier 44 thus permitting the various signals detected on the surface of the skin of the patient 46 to be applied via the leeds 48 and the EKG amplifier 44 to the microprocessor 40. In addition, the output of the transistor Q3 is also applied via operational amplifier 82 to energize transistor Q4, whereby a further supply voltage $V_A$ is developed to be applied to various components of the system of FIGS. 7A, B and C including the keyboard decoder 52, the display driver 72, the battery checker 46 and the LEDs of the array 58. Further, a voltage is applied to a timing circuit comprises of resistor R12 and capacitor C4 whereby a signal is developed at C1 after a time interval dependent upon the values of resistors R12 and C4. Thus, initially, a self-checking program is run upon the initial energization of the system of FIG. 7, i.e., the first time that the switch 22-1 is energized. Thereafter, the signal appearing at C1 is high to thereby avoid the execution of the checking routine as will be explained in detail later. The last described state or mode of operation is the Power Down state. In this state, the processors notably the microprocessor 40, the I/O expander 56, the latches 56a and 56b and the EPROM 82 as well as the beeper 60, remain denergized thus reducing the drain upon the batteries BT1 and BT2.

The third or operating mode is entered when the operator depresses a selected portion or key of the keyboard, whereby one of the decoders 52a or b of the keyboard decoder 52 is actuated to transmit from its data available DA output terminal a corresponding signal to the power control circuit 80 and in particular via a level shifter 84 to set the power down flip/flop 54a, whereby the power control circuit 80 disposes the system seen in FIGS. 7A and B from its power down to its operating mode. In particular, the output from the Q terminal of the power down flip/flop 54a goes high and is applied via resistor R6 to render conductive transistor Q12 to develop output voltages $V_B$. As a review of FIG. 7B will indicate, the energizing voltage $V_B$ is applied to energize each of the microprocessors 40, the latches 68a and 68b, the EPROM 82 and the I/O expander 56, noting that these elements require higher levels of energization and it is desired to maintain these elements in an unenergized state except when they are operative.

Finally, the power control circuit 80 is reset by signals applied via the entry points D and E and the corresponding level shifters 86 and 88 to reset terminals respectively of the power down flip/flop 54a and the master flip/flop 54b. The signals applied through entry points D and E are developed by the latch 68b as the program or processes is executed. As will become apparent from the description of the process or program as described with respect to FIGS. 8A-L, the control process resets the power control circuit 80 at various points in its operation in order to minimize the power drain imposed upon the batteries BT1 and BT2.

In the measure mode of operation as entered by depressing the MEAS key 26-11 as will be explained with respect to FIGS. 8J and K, a signal is taken from the electrodes attached to the skin of a patient 46 and applied via electrodes 48a, b and c, to the EKG amplifier 44 and in particular to its shaping and amplifying circuit 90. Briefly, the circuit 90 shapes, clips and amplifies the detected artifact and PIP pulses to apply pulses of a given amplitude and corresponding pulse width to the interrupt input INT of the microprocessor 40. As shown in FIG. 7, a series of diodes CR1 to CR6 are connected to the leeds 48a, b and c to provide defribrilation protection. Further, the amplified signal is differentiated by a differentiator comprised of resistor R5 and capacitor C6 to sharpen the spikes as amplified by transistor Q1 before being applied to the interrupt input INT of the microprocessor 40. In this simple manner, the measure mode may be effected without the use of an input/output circuit to time multiplex or otherwise process the EKG and PIP signals.

Briefly, in the measure routine, the interval between the two spikes of the EKG signal is measured by down counting a first counter within the microprocessor 40, which count is terminated upon the arrival of the second of the EKG signals, i.e., the leading edge of the second EKG signal. Further, upon the occurrence of the leading edge of the second EKG signal in the series, a second counter within the microprocessor 40 is initiated to count the time interval corresponding to the pulse width of the artifact signal to thereby provide an indication of its pulse width.

Figure 8A:
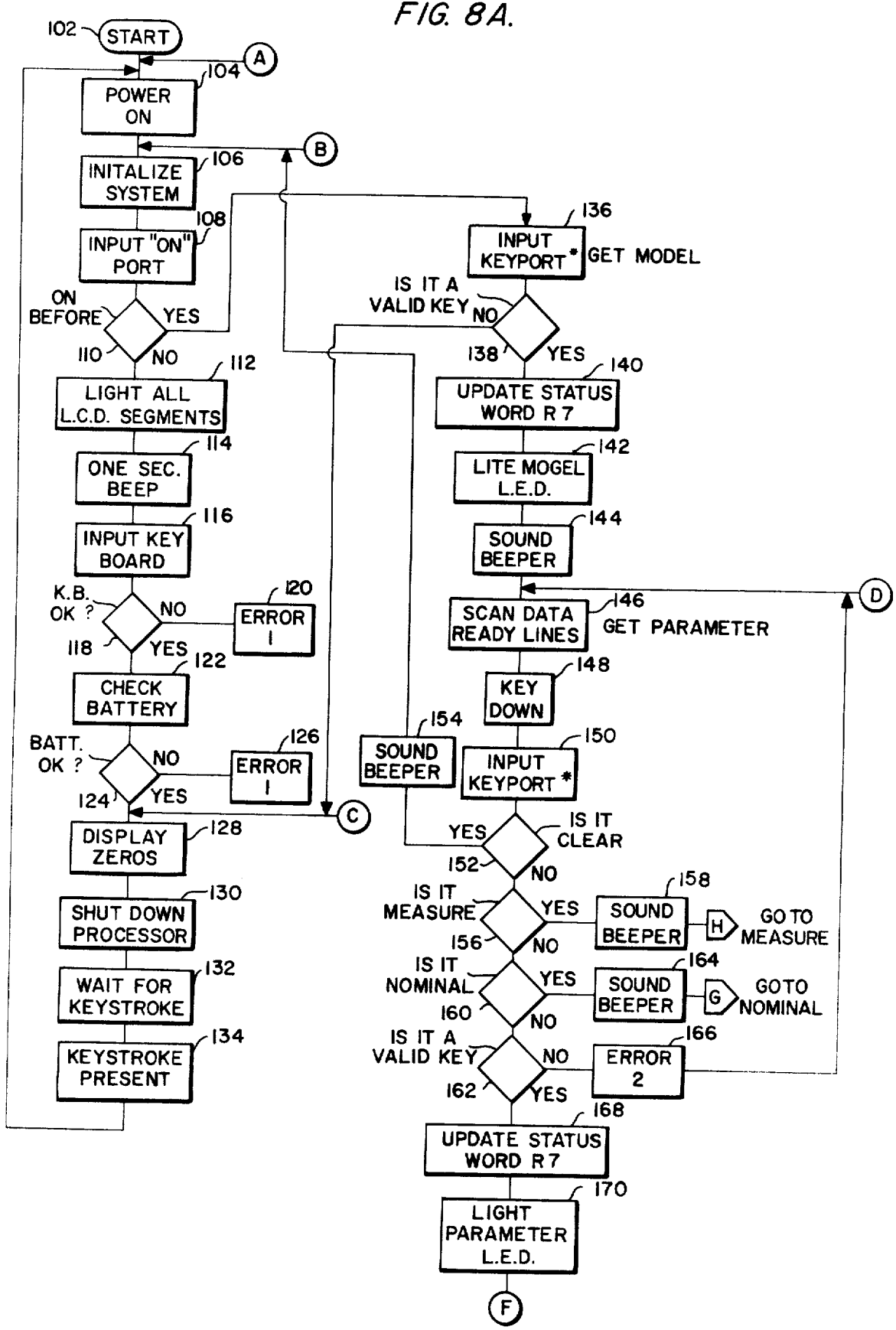
Figure 8B:
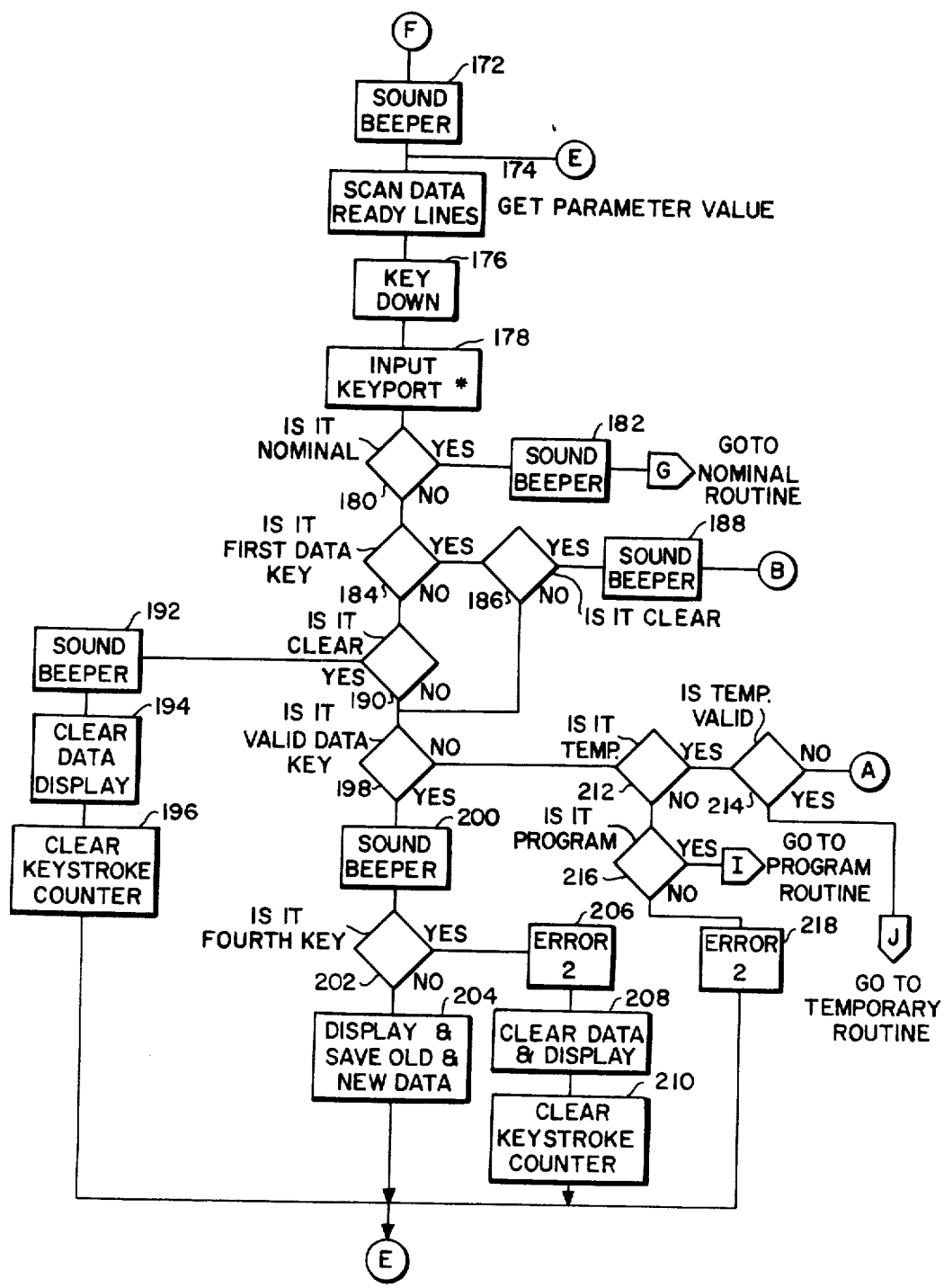
Figure 8C:
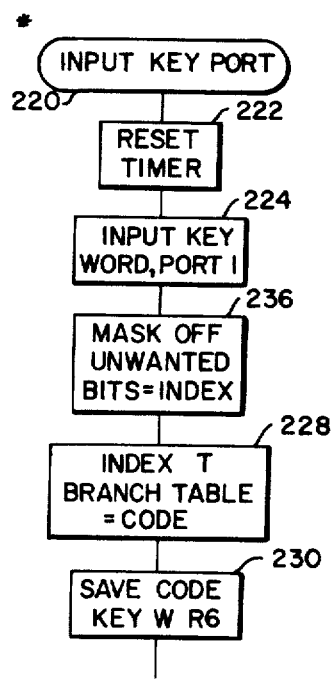
Figure 8D:
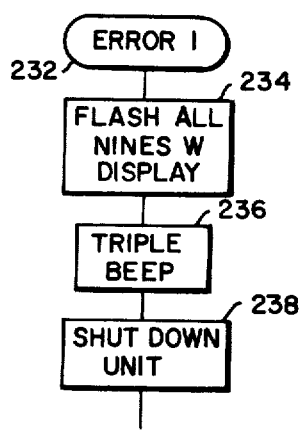
Figure 8E:
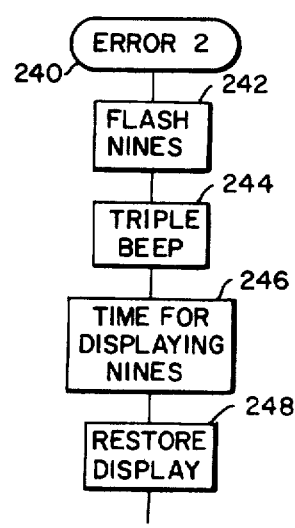

Referring now to FIG. 8A to 8L, there is shown a flow diagram of the process and its routines as stored within the memories of the microprocessor 40 and the EPROM 82 and executed by the microprocessor 40 to effect the programming and transmitting of the parameters to the pacemaker 16, as well as to supply control signals to the power control circuit 80, whereby the system of FIG. 7 is set to various operating modes, i.e., off/rest, power down, operating or transmitting. Referring specifically to FIG. 8A, the process enters via the start-step 102 to determine by step 104 if the on/off switch 22-2 has been actuated and if so, the system is initialized in step 106, i.e., parameters are loaded into a RAM (not shown) of the microprocessor 40; in particular, all zeros are written to the first sixteen bytes of the RAM while one's are written in those locations corresponding to the ports P10 to P17, and P20 to P27 of the microprocessor 40 whereby these ports are enabled to receive data. Next, step 108 checks to determine whether a high voltage appears at the restart terminal C indicating that the system has been initialized, i.e., a voltage has previously charged the capacitor C4 as explained above. As shown in FIG. 7, the high voltage is applied via the terminal C to the input port P60 of the I/O expander 56, whereby it is applied to the microprocessor 40. In step 110, the process determines whether it has been on before and if not, the process proceeds to step 12, whereby the display driver 72 energizes all the segments of the liquid crystal display 28 i.e., all "888" are displayed. Thereafter, the beeper or transducer 60 is energized to provide a one second beep in step 114 before a check is made in step 116 to determine whether any of the conductive lines of the keyboard are shorted together. If so, a one appears on the DA lines connected to each of the encoders 52a and 52b of the keyboard decoder 52 and applied thereby to the microprocesssor 40. Step 118 determines whether there is a short and if so, an exit is made via step 120 to the first error subroutine as shown in FIG. 8D. First, in step 234, the display driver 72 energizes the liquid crystal display 28 to display all "999" before actuating the beeper 60 to provide three short beeps. Thereafter, step 238 shuts the entire system down. In particular, the microprocessor 40 causes the latch 68b to apply a "one" signal via its output line 6 to the D input of the power control circuit 80, whereby an enabling signal is applied through the level shift 86 to reset the master flip/flop 54b, whereby the system as shown in FIG. 7 is disposed to its power down mode.

If in step 118 as shown in FIG. 8A, it is determined that there are no shorts in the keyboard, the process moves to step 122 where the outputs appearing at the terminals K and L of the battery checker 46 are applied via the input/output expander 56 to the microprocessor 40, whereby it is determined whether these outputs are greater than predetermined levels. The battery check step 122 is more completely shown in the subroutine of FIG. 8F, which enters via point 250 to examine in step 252 the voltage appearing at the K terminal of the battery checker 46, comparing this voltage with a first level, e.g., 6.9 volts, below which the system may not be safely operated to program and transmit encoded signals to the pacemaker 16. If the voltage level of the batteries is below this first level, the process exits via step 256 to the first error subroutine as shown in FIG. 8D, whereby the entire system is shut down. If the battery voltage level is above the first level, a check is made of the voltage level appearing at terminal L of the battery checker 46, whereby that voltage is compared with a second level e.g., 7.4 volts, and if less, a signal in the form of a flag is set into a battery condition register within the microprocessor 40, to indicate in a manner to be explained, that the battery voltage is low, i.e., that a limited number of program cycles may be run before the system will be shut down. If the voltage is above the second level, the system returns to the process as shown in FIG. 8A, and step 128 causes the display driver 72 to display "000" upon the liquid crystal display 28, before shutting the processors down in step 130. In particular, the microprocessor 40 develops through its latch 68b a one to the E input of the power control circuit 80 to apply a signal to the reset input of the power down flip/flop 54a, whereby the system is disposed in its power down mode, i.e., the power signals are removed from each of the processors 68a, 68b, 82 and 40 to thereby conserve the batteries BT1 and BT2. At this point, the system waits in step 132 for one of the keys of the keyboard to be depressed and upon its actuation, as detected in step 134, a one signal appears upon one of the DA lines of the decoders of the keyboard decoder 52, to be applied to the microprocessor 40, and via the level shifter 84 to set the power down flip/flop 54a, whereby energizing signals are applied to the processors of the programmer system.

At this point, the process returns to steps 104 and 106. Again, step 108 looks to determine whether a high signal is at the restart terminal C indicating that the system was previously initialized and that the checks of steps 116 and 122 have been successfully performed. In step 110, if the system had been initialized "on"before the process moves to step 138 whereby the input of the keyboard is checked, i.e., the output of the keyboard decoder 52 is examined to determine whether a valid key has been struck. At this point in the process, the system is only able to accept those inputs indicating that a particular pacemaker 16 is to be programmed. In other words, only one of the keys 22-1 and 22-3 and 22-4 may be actuated, while if any other key is actuated it will be ignored. More specifically, step 136 examines the particular output of the keyboard indicating that a particular key has been actuated and compares that output to determine by step 138 whether there is an appropriate match indicating that one of the keys 22-1, 22-3 or 22-4 has been actuated, and if so, the process moves to step 140. If not, the step moves to step 128 to continue as described before.

In step 140, the signal as derived from the keyboard decoder 52 is compared by the microprocessor 40 with a table stored in a ROM of the microprocessor 40 to identify the particular model of programmer that has been selected, whereby a signal indicative of the model is stored within the R7 register of the microprocessor 40. Thereafter, a LED of the array 58 corresponding to the depressed key is energized in step 142 and the beeper 60 is energized to give a single short beep. In step 146, the microprocessor 40 waits for the next key of the keyboard to be depressed, whereby a data ready signal is applied to the microprocessor. In step 148, the microprocessor 40 responds thereto to transmit an output pulse to the OE input of each of the decoders 52a and 52b.

At this point, the process is ready to identify the particular parameter to be programmed and executes step 150, which is more fully shown by the subroutine of E FIG. 8C and is entered via step 220. In step 222, a timer in the form of a counter within a PROM of the microprocessor 40 is set to time for a period of 15 seconds, i.e., the time interval in which the operator has to actuate the appropriate parameter key. Upon depressing of a key, the signals derived by the keyboard decoder are applied to port 1 i.e., the inputs P10 and P17. Noting that only 4 bits are needed to identify this particular key, step 226 masks off the undesired other 4 bits of the input signal. Next, in step 228, the process identifies which of the decoders 52a, or 52b has forwarded the signal and adds a signal from a "branch table" identifying that decoder, to the index signal indicative of the key that was depressed to thereby provide a code indicating which of the available keys was depressed. It is noted that each of the decoders 52a and 52b will provide the same index signals for different keys and it is therefore necessary to identify the decoder 52a or 52b from which the signal originates in order to identify the depressed key. Next, in step 230, the code word identifying the depressed key is stored in a temporary register R6 of the microprocessor 40. As will be evident from the following discussion, the R6 register is a designated storage location within the microprocessor 40 where a value may be reviewed and compared.

Figure 8F:
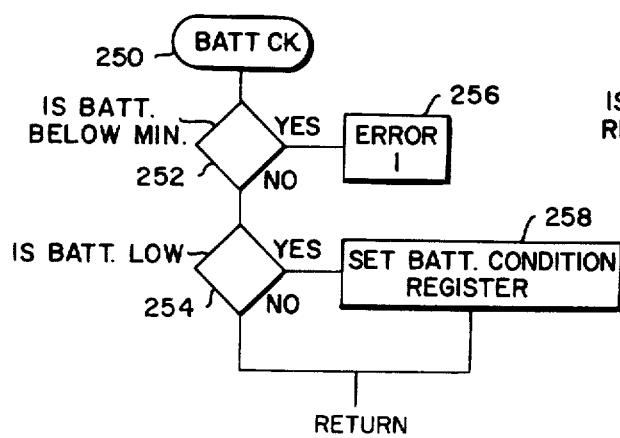
Figure 8L:
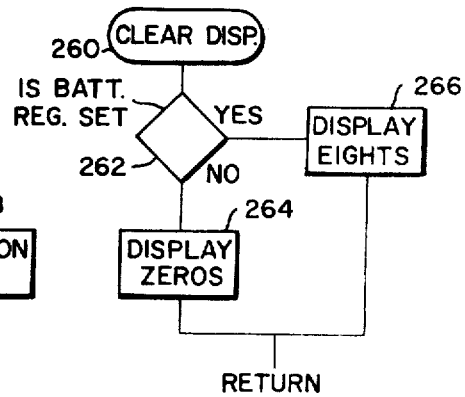
Figure 8G:
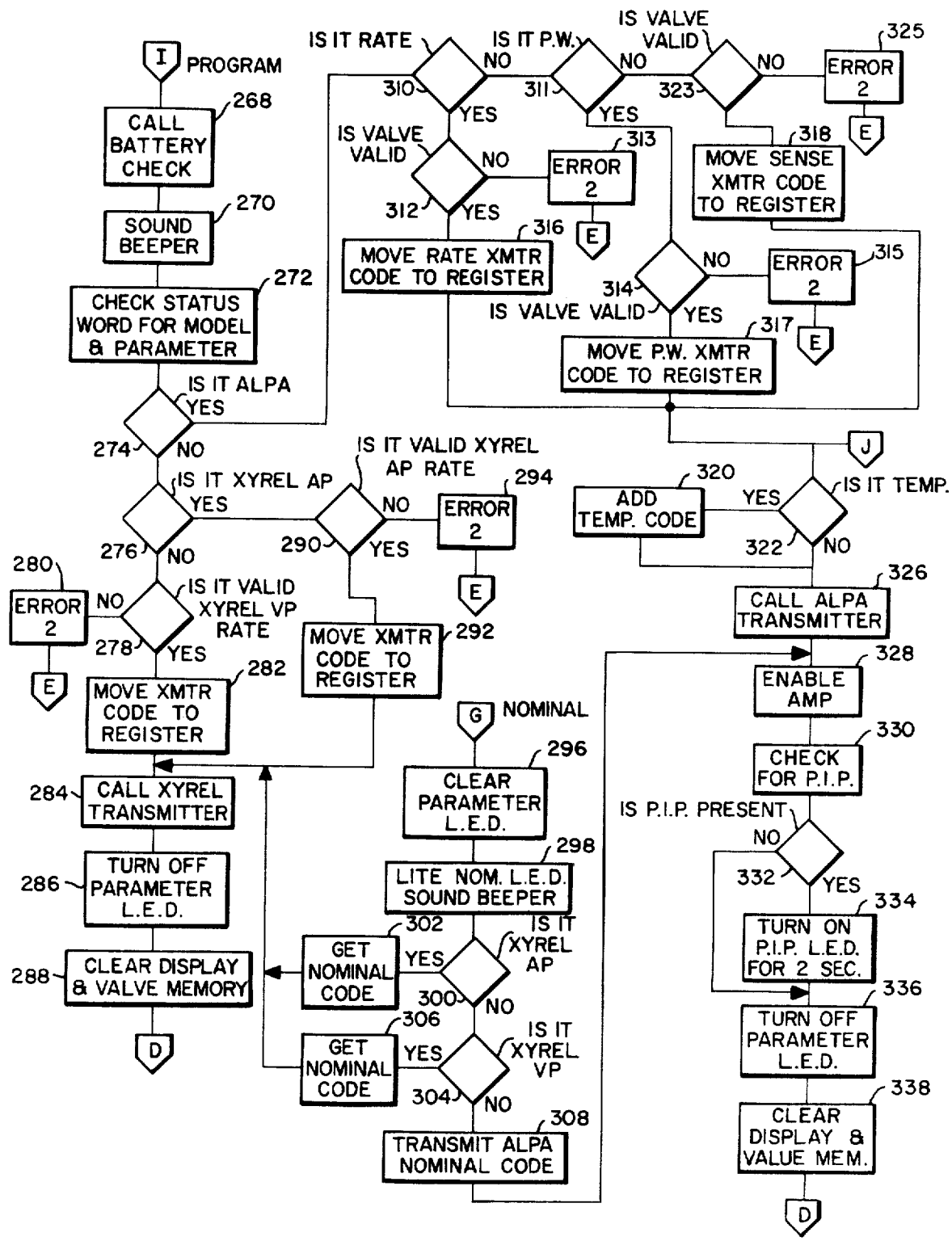

The process continues in step 152 to determine whether the signal in register R6 indicating the key that has been depressed is the clear key and if so, the beeper 60 is actuated in step 154 before returning via entry point B to step 106. If the clear button has not been depressed, the process moves to step 156 wherein the register R6 is again examined to determine whether the MEAS key 26-11 has been depressed and if so, the process exits after sounding the beeper 60 in step 158 to the measure subroutine as shown in FIGS. 8J and 8K. In step 160 the process determines whether the NMNL (Nominal) key 26-3 has been depressed and if so, the beeper 60 is energized in step 164 before exiting to the nominal subroutine via entry point G as shown in FIG. 8G. Thereafter in step 162, the process examines designated bits of the stored word in register R6 to determine if the depressed key is valid, i.e., the key is one of the following keys: rate key 22-7, the PW key 22-8, the SENSE key 22-9, the MNNL key 26-3, the TEMP key 26-2, or the MEAS key 26-11. If valid, the status word stored within the R7 register is updated to indicate the particular parameter as now stored therein. In particular, the R7 register is an eight bit register four bits identifying the particular model of the pacemaker 16 to be programmed and four bits identifying the parameter that has been chosen. Thereafter in step 170, the corresponding LED of the array 58 is energized, before moving through transfer point F to the routine shown in FIG. 8B.

As the process enters via transition point F as shown in FIG. 8B, the beeper 60 is sounded in step 172 indicating that a parameter has been selectively entered for programming. Thereafter, the process waits in step 174 for the next key to be depressed indicative of a particular value of the parameter, i.e., the occurrence of a data available DA signal upon the corresponding output of one of the decoders 52a and 52b. Upon the occurrence of such a signal, step 176 applies an output enable signal OE to the keyboard decoders. In step 178 as more specifically shown in FIG. 8C, the particular key and its parameter is identified and stored within the R6 register of the microprocessor 40. Next, step 180 determines whether the depressed key is the nominal NMNL key 26-3 and if so, the beeper 60 is sounded in step 182 before transferring via entry point G to the nominal subroutine of FIG. 8G. Next, in step 184, the bits of the signal stored in the register R6 are examined to determine whether the depressed key is a "0" to "9" or clear key and further, if that is the first key so actuated. If yes, step 186 determines whether it is the clear key and if so, the process moves to step 190 where it is determined whether the depressed key is the clear key and if yes, the beeper is sounded in step 192 before clearing that digit from the display 28 by step 194 and resetting the key stroke counter in step 196. As will become evident, the arrangement as described permits entry of only three digits to be stored and to be displayed upon display 28. If the operator decides the entered value is not appropriate, he may simply depress the clear key whereby the misentered digit is erased by steps 192, 194 and 196. If however, no previous key indicative of a parameter value has been entered, the system returns to the beginning of the routine i.e., step 106 as shown in FIG. 8A.

Next, step 198 determines whether the depressed key is valid, i.e., a "0" to "9" key, and if not, step 212 determines whether it is the TEMP key 26-2. If a TEMP key, step 214 determines whether the pacemaker to be programmed is the alpha pacemaker and if so, exits via point J to the routine as shown in FIG. 8G. In this regard, it is noted that of the pacemakers to be programmed by the programmer 12 in the illustrative embodiment of this invention, only the alpha programmer is capable of being programmed in a temporary mode. If the depressed key is not a temporary key as decided in step 212, the process in step 216 determines whether the PROGRAM key 26-1 has been depressed and if so, exits via transition point I to the transmitting or program routine as shown in FIG. 8G. If the program key 26-1 has not been depressed, an error condition is indicated by step 218 whereby the display flashes "999" and the transducer 60 provides three beeps before returning to the beginning of the routine as shown in FIG. 8B.

As the operator actuates a parameter key, step 202 determines whether a fourth parameter key has been actuated by examining the key stroke counter noted before. In this regard, each of the values of the parameters to be entered may be expressed by only three digits; therefore, if the operator attempts to enter a fourth digit, operator error will be indicated in step 206 by appropriate actuation of the display 28 and the beeper 60, before clearing that data from its memory and its display 28 in step 208 and clearing the key stroke counter in step 210 before returning to the beginning of this routine as through entry point F. If the depressed numerical key is not the fourth key, i.e., it is either the first, second or third key, step 204 displays the entered digit and places the new data into storage along with the previously entered data, before returning to the beginning of the routine through entry point E to accept the next piece of data to be entered via the keyboard. Thus, the process will first enter data indicating which pacemaker 16 is to be programmed, then the parameter to be programmed and then the value of the parameter so programmed. At this point, the process is ready for the operator to depress the program button 26-1 to enter the program or transmitting routine as shown in FIG. 8G. If after the entry of data, the operator fails to press the program key 26-1, the system will provide an error indication and will permit the operator to again actuate the program key 26-1.

Referring now to FIG. L, there is shown a subroutine that occurs each time a step indicates that the display 28 should be cleared and is entered via step 260. At that point, step 262 examines the battery condition register of the microprocessor 40 to determine whether a flag or indication has been set indicating that the battery voltage is low, as was previously determined by step 254 as shown in FIG. 8F. If yes, step 266 causes the display 28 to display "888" whereby the operator is informed that the condition of the batteries BT1 and BT2 is below the second level indicating that the batteries are low but are sufficient for a relatively short period of time to continue to encode and transmit the signals to the pacemaker 16. At this point, the operator should attend to replacing the batteries BT1 and BT2 of the programmer 12 to insure its continued operation. If step 262 determines that the battery voltages above the second level, "000" is displayed by step 264 on the display 28 indicating that the battery level voltage is satisfactory.

When the PROGRAM key 26-1 is depressed as detected by step 216, the process exits to the program or transmit routine as shown in FIG. 8G, where initially step 268 checks the condition of the batteries in a manner more specifically shown with respect to FIG. 8F, and if satisfactory, step 270 actuates the beeper 60 for a single beep. At this point, the routine must determine which of the three pacemakers the programmer 12 is to program by checking in step 272 the status register R7 of the microprocessor 40 to identify the particular pacemaker 16 and the parameter to be programmed. In step 274, the data in register R7 is reviewed to determine whether it is indicative of the alpha pacemaker and if yes, the process proceeds to step 310. In this regard it is noted that the programmer 12 is capable of programming an alpha pacemaker 16 with four parameters namely the rate, pulse width, the sensitivity of the pacemaker sensing amplifier and temporary. Bu contrast, the XYREL AP and XYREL VP pacemakers may be only programmed as to the rate of pacing. First, describing the programming of the alpha pacemaker, step 310 examines the R7 register to determine whether it is the rate parameter to be programmed. If not, step 311 examines the R7 register to determine whether the parameter is the pulse width to be programmed and if not, then it is known that the parameter to be programmed is sensitivity, and at that point the process obtains from a truth table within an EPROM of the microprocessor 40, the sense transmitter code indicating that the sense parameter is to be programmed for the alpha pacemaker 16; this sense transmitter code is then stored in the accumulator register within the microprocessor 40. Next, step 323 determines whether the value of the sensitivity that has been entered is a valid value thereof in accordance with table 1 set out above, by comparing the value entered within the register R7 with the limits obtained from that truth table stored within the EPROM of the microprocessor 40. If the value is not valid, step 325 provides an error manifestation by energizing the visual display 28 and the beeper 60 in accordance with the subroutine of FIG. 8E. If the pulse width parameter is to be programmed, step 314 determines whether the selected value is valid and if not, a similar error manifestation is made by step 315; if valid, the pulse width transmitter code for the alpha pacemaker is shifted to the accumulative register of microprocessor 40. If the rate is to be programmed as determined by step 310, its value is compared with the noted truth table to determine whether it is within accepted limits and if not an appropriate error manifestation is made in step 313. If valid, the rate transmitter code for the alpha pacemaker 16 is sent to the accumulative register of the microprocessor 40.

As explained above, if the TEMP key 26-2 has been depressed, a corresponding flag is stored in the appropriate register and the process enters the routine shown in FIG. 8G via point J. At this point in the process, step 322 determines whether the TEMP flag has been set and if yes, a TEMP code is also programmed to be transmitted to the pacemaker 16, whereby the TEMP code is programmed in the memory of the pacemaker 16. As indicated above, the pacemaker 16 will continue to operate in the programmed temporary mode as long as the programmer 12 is held sufficiently close so that the pacemaker's reed switch is continued to be held closed, or until the program key 26-1 is actuated whereby a permanent set of parameters is transmitted and stored within the pacemaker's memory.

At this point in the process, the encoded signals are transmitted by step 326 to the alpha pacemaker 16. As shown in FIG. 4, the encoded signals include data indicative of the parameter, the value of the parameter, an access code and a parity code. To this end, the microprocessor 40 includes four registers for receiving date corresponding to each of these four parts of the transmitted signal. Thus, in step 326 data identifying the parameter being coded is disposed in the first register, whereas the parameter's value is stored in a second register. Step 326 determines the appropriate access code for the alpha transmitter, disposes the code in a third register and calculates the parity code to be disposed in a fourth register. Thereafter, the microprocessor transmits the encoded data from each of the registers in succession.

After the transmission of data, step 326 enables the EKG amplifier 44 and in particular enables the data therefrom to be entered via the interrupt input INT to the microprocessor 40. Thereafter step 330 determines whether a PIP pulse has been received by detecting the artifact and PIP pulses as applied to the interrupt INT. Step 332 determines whether the PIP pulse has occurred within the range of PIP intervals after the artifact pulse and whether its width is within acceptable PIP limits; if yes, step 332 turns on the LED of the array 58 disposed behind the PIP portion of the keyboard. Thereafter step 336 turns off the PIP LED after approximately 2 seconds, and step 338 clears the display 28 and the value so programmed from the RAM in the microprocessor 40, before transferring via transition point D to the routine as shown in FIG. 8A.

Returning now to step 274, if it is determined that the alpha pacemaker is not to be programmed, step 276 examines the status register R7 of the microprocessor 40 to determine whether the XYREL pacemaker AP is to be programmed and if so, the value of the program rate is checked with a truth table within the EPROM of the microprocessor 40 and if valid, the rate transmitter code for XYREL AP pacemaker is moved to the accumulator register in step 292. If the XYREL AP rate is not valid, an error manifestation is made in step 294. If as determined by step 276 a XYREL VP pacemaker is to be programmed, step 278 determines whether the XYREL VP rate as initially programmed is a valid rate as by comparison with a truth table within the ROM of the processor 40; if valid, the rate transmitter code for the XYREL VP pacemaker is transferred to the accumulator register in step 282. If the rate selected is not a valid rate, an error manifestation is made in step 280. At this point, the system calls the XYREL transmitter in step 284, whereby the transmitter code is disposed within a register of the microprocessor 40 and a series of bursts programmed dependent upon the selected value of rate is transmitted by the transmitter 42 to the XYREL pacemaker 16. At that point, step 286 turns off the LED of the array 58 corresponding to the rate parameter and the value of the rate parameter is cleared from display 28 and from the corresponding memory of the microprocessor 40 in step 288, before returning the process via transition point D to the routine as shown in FIG. 8A.

If the nominal NMNL key is depressed as detected in step 160 of FIG. 8A, the process exits via the point G as shown is FIG. 8G, whereby the LED identifying the parameter is first cleared in step 296 and thereafter, the LED of the array 58 corresponding to the NMNL key 26-3 is energized. Thereafter in step 300, register R7 of the microprocessor 40 is examined to determine whether the XYREL AP pacemaker has been programmed and if so, step 302 obtains a code in accordance with the nominal rate stored within the external EPROM 82, to be transmitted by step 284. In step 304 it is determined whether the XYREL VP pacemaker has been programmed and if so, step 306 obtains the nominal rate code to be transmitted by step 284. It is understood that if the alpha programmer is to be programmed, as determined by a no decision of step 304, it is then necessary to obtain the nominal coded values for each of the nominal alpha parameters including rate, pulse width, sensitivity, amplitude output of the pacing pulse, the refrectory period, hysteresis and demand mode. In particular, step 308 obtains the nominal codes for each of these parameters and sequentially transmits one parameter at a time, until each of the eight nominal values of these parameters have been programmed into the alpha pacemaker.

Figure 8J:
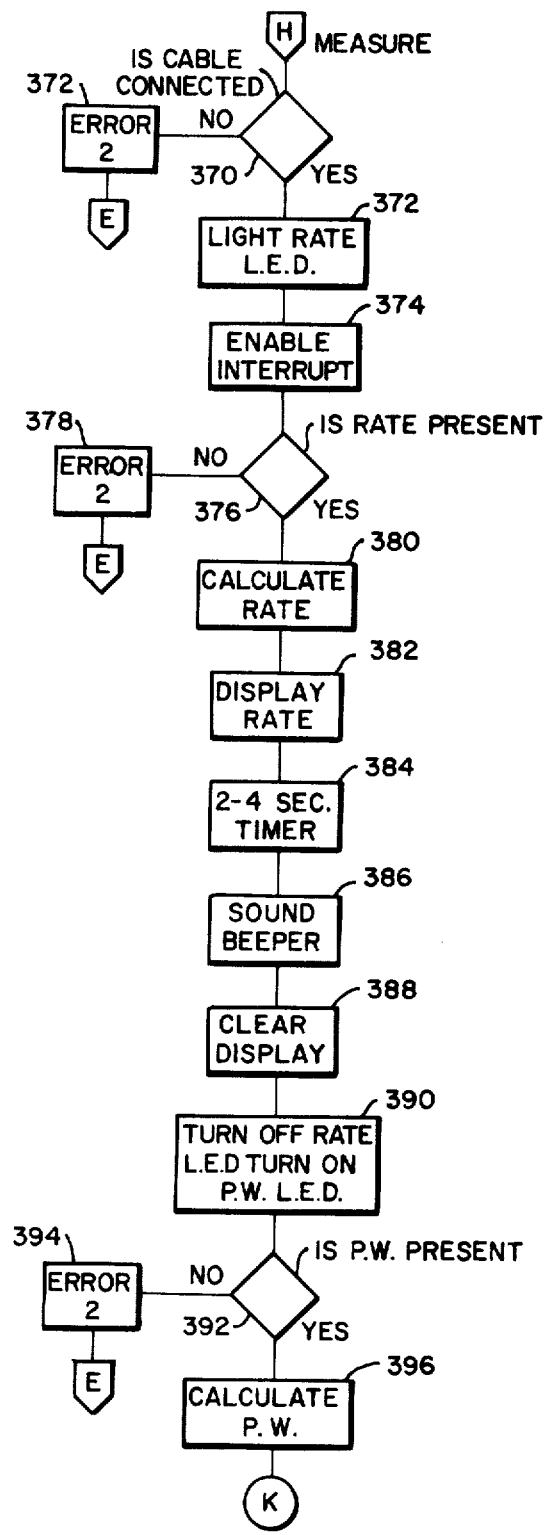
Figure 8K:
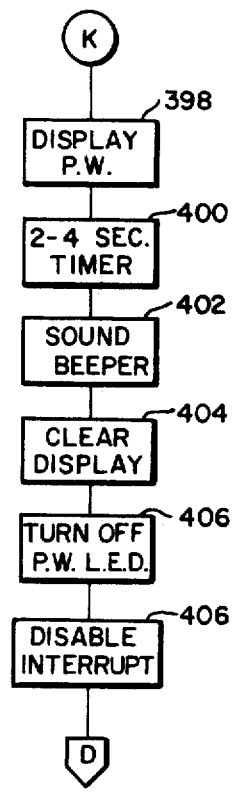

If the MEAS key 26-11 has been depressed as detected in step 156, the process transfers through transition point H to the measure routine as shown in FIGS. 8J and K. First, step 370 examines terminal M to determine whether the cables 48a, b and c are coupled to the programmer 12 and if not, an appropriate error manifestation is made in step 372. If connected, step 372 actuates the LED of the array 58 disposed behind the RATE key 22-7 to be lighted, and step 372 enables the interrupt input INT of the microprocessor 40. Thereafter, step 376 looks for the occurrence of first and second artifact pulses as applied via the EKG amplifier 44 to the interrupt input INT of the microprocessor 40. If the artifact pulses are not present, an error manifestation is made in step 378. If the first and second artifact pulses are detected, step 380 sets and resets a first counter within the RAM of the microprocessor 40 to determine the interval therebetween, and notes the count of the first counter to calculate the pulse rate. Next, an indication of the pulse rate as calculated in step 380 is made upon the display 28 in step 382. Step 384 sets a timer to time a period of 2 to 4 seconds and if that period expires without the detection of an artifact pulse, step 386 energizes the beeper 60, and the display 28 is cleared in step 388. Thereafter the LED of the array 58 disposed behind the RATE key 22-7 is deenergized and the LED corresponding to the PW key 22-8 is energized. Thereafter step 392 examines whether the second artifact pulse has been received and if yes, step 396 sets and resets a second counter within the RAM of the microprocessor 40 to measure the pulse width of the artifact pulse generated by the pacemaker 16. If the second pulse is not present, an error manifestation is made in step 392.

At this point as shown in FIG. 8K, the process transfers to step 398, wherein a value of the pulse width is displayed upon the display 28. Step 400 sets a counter to time for four seconds and thereafter in step 402 sounds the beeper 60 and clears display 28 before step 406 turns off the LED associated with the PW key 22-8. Finally, step 408 disables the interrupt input INT, before returning via transition point D to step 146 of the routine as shown in FIG. 8A to sense the next key to be depressed by the operator.

We claim:

1. A computer system energized by a depletable energy source coupled to selectively energize the elements of said computer system, said computer system operable in an off/rest mode, a power down mode, and an operating mode, comprising:
   (a) data input means for entering data into said computer system;
   (b) decoding means coupled to said data input means and operable in the power down mode for decoding data received from said data input means and for providing a data available manifestation indicative of the availability of decoded data;
   (c) actuatable means for providing upon actuation a transition manifestation;
   (d) memory means for storing a program;
   (e) processor means energized in its operating mode for executing the program to process the decoded data derived from said decoding means; and
   (f) power control means coupled to said actuatable means and to said depletable energy source for variously energizing the elements of said computer system in its off/rest mode at a low power level, its power down mode at an intermediate power level, and its operating mode at a high power level, said power control means comprising a storage element continuously energized by said depletable energy source and responsive to the transition manifestation of said actuatable means to dispose said computer system from its off/rest mode to its power down mode wherein said decoding means is energized by said depletable energy source, said power control means coupled to said decoding means and responsive to the data available manifestation to dispose said computer system from its power down to its operating mode, wherein said processor means is energized to execute the stored program.

2. The computer system as claimed in claim 1, wherein said data input means comprises a key board of plurality of actuatable keys.

3. The computer system as claimed in claim 2, wherein said decoding means is responsive to the actuation of a key of said key board to generate and apply its data available manifestation to said power control means, whereby said power control means disposes said computer system from its power down mode to its operating mode.

4. The computer system as claimed in claim 1, wherein said computer system further comprises display means for providing an indication of the operation of said computer system, said display means being deenergized in said off/rest mode and being energized in said power down and operating modes.

5. The computer system as claimed in claim 1, wherein there is included energy source checking means being coupled to said depletable energy source to determine its power output level, said processor means operative to compare the energy source level with a predetermined minimum level below which said computer system may not operate and if below said minimum level, said power control means disposing said computer system to its off/rest mode.

6. The computer system as claimed in claim 2, wherein said decoding means is responsive to the closing of a key of said keyboard, said power control means coupled to said decoding means for determining whether one of said keys is inadvertently closed and if so, for disposing said computer system from its power down to its off/rest mode.

7. The computer system as claimed in claim 1, wherein the program stored within said memory being designed to receive and process data from said input data means in a predetermined sequence, said processor means responsive to data inputted from said data input means to compare the inputted data with that data that may be accepted at a point in the execution of said program and if not acceptable, providing a manifestation to said power control means, whereby said power control means is disposed from its operating mode to its power down mode.

8. The computer system as claimed in claim 7, wherein said data input means comprises a keyboard including a plurality of actuatable keys, said decoding means responsive to the actuation of a key to provide a manifestation of the depressed key, said processor means coupled to said decoder means to determine whether the depressed key is acceptable and if not for applying said manifestation to said power control means, whereby computer system is disposed from its operating mode to its off/rest mode.

9. The computer system as claimed in claim 8, wherein said memory stores a truth table identifying the acceptable keys that may be depressed.

10. The computer system as claimed in claim 9, wherein said processor means is responsive to the actuation of one or more keys to provide a manifestation of the value of the inputed data and comparing the value manifestation with acceptable values that may be input into said computer system, said processor means responsive to an unacceptable value for providing an error manifestation to said power control means to dispose said computer system from its operating mode to its power down mode.

11. The computer system as claimed in claim 1, wherein said computer system is further operable in a transmit mode, said processor means operable in its operating mode for executing the program to process the data to be transmitted and thereafter for providing a transmit ready manifestation to initiate the transmit mode, said depletable energy source includes first and second batteries, said power control means comprising switch means normally disposed in a first position connecting said first and second batteries in parallel with each other to provide a first voltage signal of a first relatively low magnitude, and disposable to a second position to connect said first and second batteries in a series configuration to provide a second voltage signal of a second relatively high level, said power control means responsive to the transmit ready manifestation for disposing said computer system to its transmit mode, wherein at least one element of said computer system is energized by the second voltage signal.

12. The computer system as claimed in claim 11, wherein said computer system comprises transmitter means periodically operable to transmit signals to a distant location, said processor responsive to the operation of said transmitter to provide a manifestation to said power control circuit to dispose said switch means from its first to its second position, to supply the second voltage signal to said transmitter means.

13. Programming apparatus energized by a depletable energy source for programming a pacemaker as to its operation to control the application of its stimulating pulses to a patient's heart, the depletable energy source coupled to selectively energize the elements of said apparatus, said apparatus operable in an off/rest mode, a power down mode, an operating mode, and a transmitting mode, said pacemaker including memory means for receiving and storing signals indicative of its operation, and generator means responsive to the stored signals for providing corresponding stimulating pulses to the patient's heart, said programming apparatus comprising:

(a) a keyboard comprising a plurality of actuable keys for receiving and entering by operator manipulation data indicative of the pacemaker's operation in which to program said pacemaker;

(b) decoder means coupled to said keyboard and responsive to the actuation of a key of said keyboard to provide a manifestation of the actuated key and a data available manifestation;

(c) actuatable means for initiating upon actuation the operation of said programming apparatus;

(d) memory means for storing a program;

(e) processor means for executing said program to process the manifestation indicative of the actuated key derived from said decoder means and after processing the actuated key manifestation to provide a transmit ready manifestation;

(f) transmitter means operable in the transmitting mode for transmitting the processed operation data to said pacemaker; and (g) power control means coupled to said actuatable means and to the depletable energy source for variously energizing the elements of said programming apparatus in its off/rest mode at a low power level and a low voltage level, its power down mode at an intermediate power level and the low voltage level, its operating mode at a high power level and a low voltage level, and its transmitting mode at a high power level and a high voltage level, said power control means comprising a storage element continuously energized by said energy source and responsive to the actuation of said actuatable means to dispose said programming apparatus from its off/rest mode to its power down mode wherein said decoder means is energized by the energy source, said power control means coupled to said decoder means and responsive to the data available manifestation of said energized decoder means for disposing said programming apparatus from its power down to its operating mode, wherein said processor means is energized to execute the stored program, said power control means coupled to said processor means and responsive to the transmit ready manifestation for operating said computer system in its transmitter mode and for applying the high voltage level to said transmitter means.

14. The programming apparatus as claimed in claim 13, wherein there is included energy source checking means adapted to be coupled to said depletable energy source to determine its power output level, said processor means operative to compare the energy source level with a predetermined minimum level below which said programming apparatus may not operate and if below said minimum level, said power control means disposing said programming apparatus to its off/rest mode.

15. The programming apparatus as claimed in claim 13, wherein the program stored within said memory being designed to receive and process data from said input data in a predetermined sequence, said processor means responsive to data inputted from said decoder means to compare the inputted data with that data that may be accepted at a point in the execution of said program and if not acceptable, providing an error manifestation to said power control means, whereby said programming apparatus is disposed from its operating mode to its power down mode.

16. The programming apparatus as claimed in claim 15, wherein said processor means is coupled to said decoder means to determine whether the depressed key is acceptable and if not for applying said error manifestation to said power control means, whereby computer system is disposed from its operating mode to its off/rest mode.

17. The computer system as claimed in claim 1, wherein there is further included amplifier means for amplifying input analog signals and operable in the power down mode as well as in the operating mode to permit a stabilization of said amplifier means during the power down mode, said amplifier means coupled to said processor means for stably amplifying and applying during the operating mode analog input signals to said processor means.

18. The computer system as claimed in claim 1, wherein said processor means executes the program stored in said memory means to provide corresponding output signals, said computer systems further including latch means coupled to receive the output signals and being responsive to selected of the output signals for providing a transfer manifestation, said power control system coupled to said latch means and responsive to the transfer manifestation for disposing said computer system from its operating mode to its power down mode.

19. The computer system as claimed in claim 1, wherein said processor means executes the program stored in said memory means to provide corresponding output signals, said computer systems further including latch means coupled to receive the output signals and being responsive to selected of the output signals for providing a transfer manifestation, said power control system coupled to said latch means and responsive to the transfer manifestation for disposing said computer system from its operating mode to its off/rest mode.

20. The computer system as claimed in claim 18, wherein said processor means includes means for providing a manifestation of the value of the data input by said data input means and for comparing the value manifestation with acceptable values that may be input into said computer system and, if not acceptable, for providing an error manifestation, said latch means responsive to the error manifestation for providing its transfer manifestation.

21. The computer system as claimed in claim 19, wherein said data input means comprises a keyboard including a plurality of actuatable keys, said decoder means responsive to the actuation of a key to provide a manifestation of the depressed key, said processor means comprising means responsive to the key manifestation to determine whether the depressed key is acceptable, and, if not, for providing an error manifestation, said latch means responsive to the error manifestation to provide its transfer manifestation.

22. The computer system as claimed in claim 18, wherein the program comprises a series of steps including a final step, said processor means executing the series of steps and for providing an end of sequence manifestation upon the execution of the final step, said latch means responsive to the end of sequence manifestation for providing its transfer manifestation.

* * * * *